United States Patent
Ueda et al.

(10) Patent No.: US 10,822,336 B2
(45) Date of Patent: Nov. 3, 2020

(54) CRYSTALS OF [2-(1-METHYL-1H-PYRAZOL-4-YL)-6(MORPHOLIN-4-YL)-9H-PURIN-8-YL] [4-(MORPHOLIN-4-YL)PIPERIDIN-1-YL] METHANONE AND PHARMACEUTICALLY ACCEPTABLE SALT THEREOF

(71) Applicant: Daiichi Sankyo Company, Limited, Chuo-ku, Tokyo (JP)

(72) Inventors: Yasushi Ueda, Shinagawa-ku (JP); Sagar Ramdas Amale, Shinagawa-ku (JP); Manjunath Govind Bhovi, Shinagawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 16/337,664

(22) PCT Filed: Sep. 28, 2017

(86) PCT No.: PCT/JP2017/035205
§ 371 (c)(1),
(2) Date: Mar. 28, 2019

(87) PCT Pub. No.: WO2018/062382
PCT Pub. Date: Apr. 5, 2018

(65) Prior Publication Data
US 2019/0225614 A1    Jul. 25, 2019

(30) Foreign Application Priority Data
Sep. 29, 2016  (JP) ................................ 2016-191168

(51) Int. Cl.
| | | |
|---|---|---|
| C07D 473/34 | (2006.01) | |
| A61P 11/00 | (2006.01) | |
| A61P 11/06 | (2006.01) | |
| A61P 19/02 | (2006.01) | |
| A61P 35/00 | (2006.01) | |
| A61P 37/06 | (2006.01) | |
| A61P 37/08 | (2006.01) | |
| A61P 37/02 | (2006.01) | |
| A61P 17/06 | (2006.01) | |
| A61K 31/5377 | (2006.01) | |
| A61P 29/00 | (2006.01) | |

(52) U.S. Cl.
CPC ........ *C07D 473/34* (2013.01); *A61K 31/5377* (2013.01); *A61P 11/00* (2018.01); *A61P 11/06* (2018.01); *A61P 17/06* (2018.01); *A61P 19/02* (2018.01); *A61P 29/00* (2018.01); *A61P 35/00* (2018.01); *A61P 37/02* (2018.01); *A61P 37/06* (2018.01); *A61P 37/08* (2018.01); *C07B 2200/13* (2013.01)

(58) Field of Classification Search
None
See application file for complete search history.

(56) References Cited

U.S. PATENT DOCUMENTS 10,174,035 B2 *  1/2019  Samby .................... A61P 19/00
2013/0102595 A1  4/2013  Bao et al.

FOREIGN PATENT DOCUMENTS

| | | | |
|---|---|---|---|
| AU | 2015268776 A1 | 1/2016 | |
| CA | 2711778 A1 * | 8/2009 | ........... C07D 487/04 |
| JP | 2012-528179 A | 11/2012 | |
| JP | 2013-525308 A | 6/2013 | |
| JP | 2014-503535 A | 2/2014 | |
| WO | 2011/130628 A1 | 10/2011 | |
| WO | 2016/157074 A1 | 10/2016 | |

OTHER PUBLICATIONS

Foster, J.G., et al., "Inhibition of PI3K Signaling Spurs New Therapeutic Opportunities in Inflammatory/Autoimmune Diseases and Hematological Malignancies," Pharmacological Reviews 64(4):1027-1054, Oct. 2012.
International Preliminary Report on Patentability dated Apr. 2, 2019, issued in corresponding International Application No. PCT/JP2017/035205, filed Sep. 28, 2017, 7 pages.
International Search Report and Written Opinion dated Dec. 5, 2017, issued in corresponding International Application No. PCT/JP2017/035205, filed Sep. 28, 2017, 17 pages.
Medina-Tato, D.A., et al., "Phosphoinositide 3-Kinase Signalling in Lung Disease: Leucocytes and Beyond," Immunology 121(4):448-461, Aug. 2007.
Murray, J.M., et al., "Potent and Highly Selective Benzimidazole Inhibitors of PI3-Kinase Delta," Journal of Medicinal Chemistry 55(17):7686-7695, Sep. 2012.
Rommel, C., et al., "PI3Kδ and PI3Kγ: Partners in Crime in Inflammation in Rheumatoid Arthritis and Beyond?" Nature Reviews Immunology 7(3):191-201, Mar. 2007.

* cited by examiner

*Primary Examiner* — Leslie A. Royds Draper
(74) *Attorney, Agent, or Firm* — Christensen O'Connor Johnson Kindness PLLC

(57) ABSTRACT

Provided are novel crystals of [2-(1-methyl-1H-pyrazol-4-yl)-6-(morpholin-4-yl)-9H-purin-8-yl][4-(morpholin-4-yl) piperidin-1-yl]methanone and a pharmaceutically acceptable salt thereof having advantageous characteristics. [2-(1-Methyl-1H-pyrazol-4-yl)-6-(morpholin-4-yl)-9H-purin-8-yl][4-(morpholin-4-yl)piperidin-1-yl]methanone and a pharmaceutically acceptable salt thereof provided by the present invention are excellent in stability and have satisfactory physical properties as a drug substance of a pharmaceutical product.

48 Claims, 26 Drawing Sheets

[Figure 1]
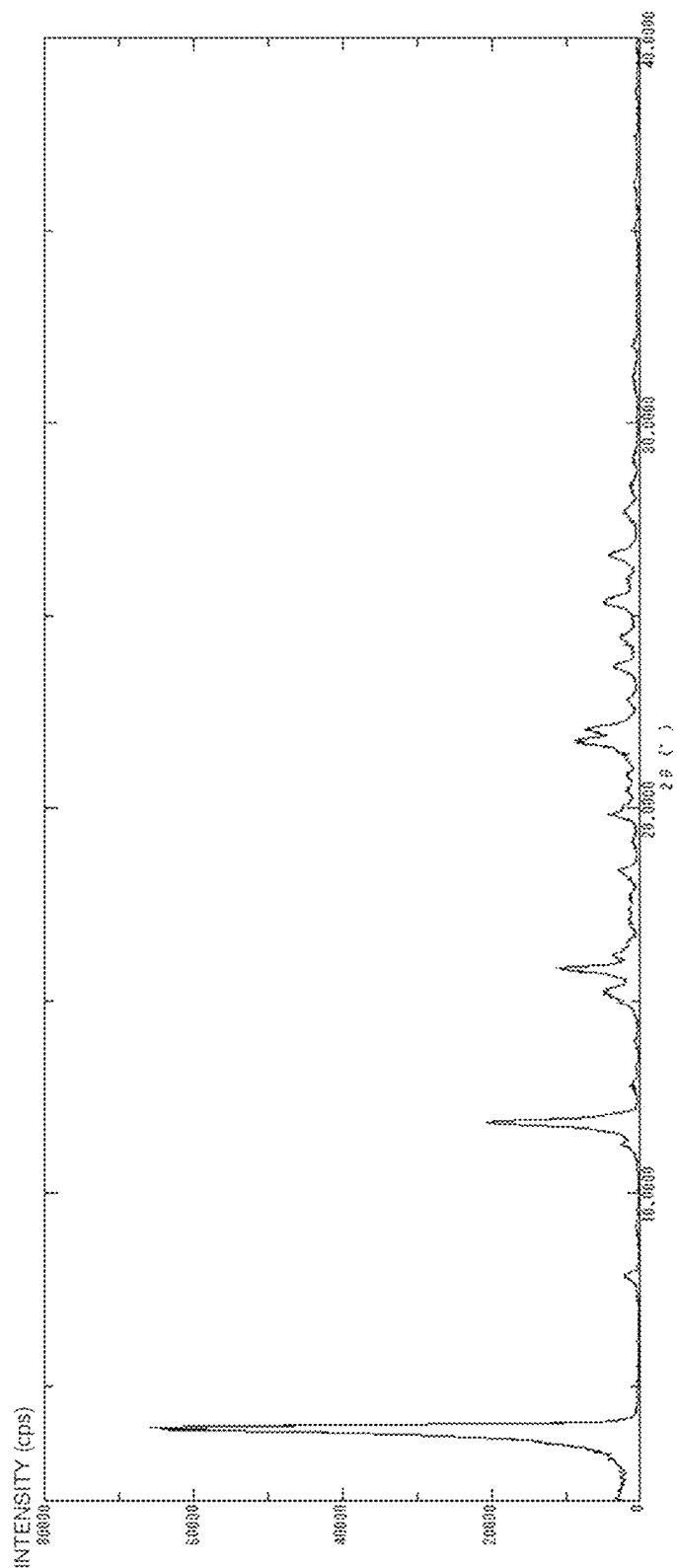

[Figure 2]
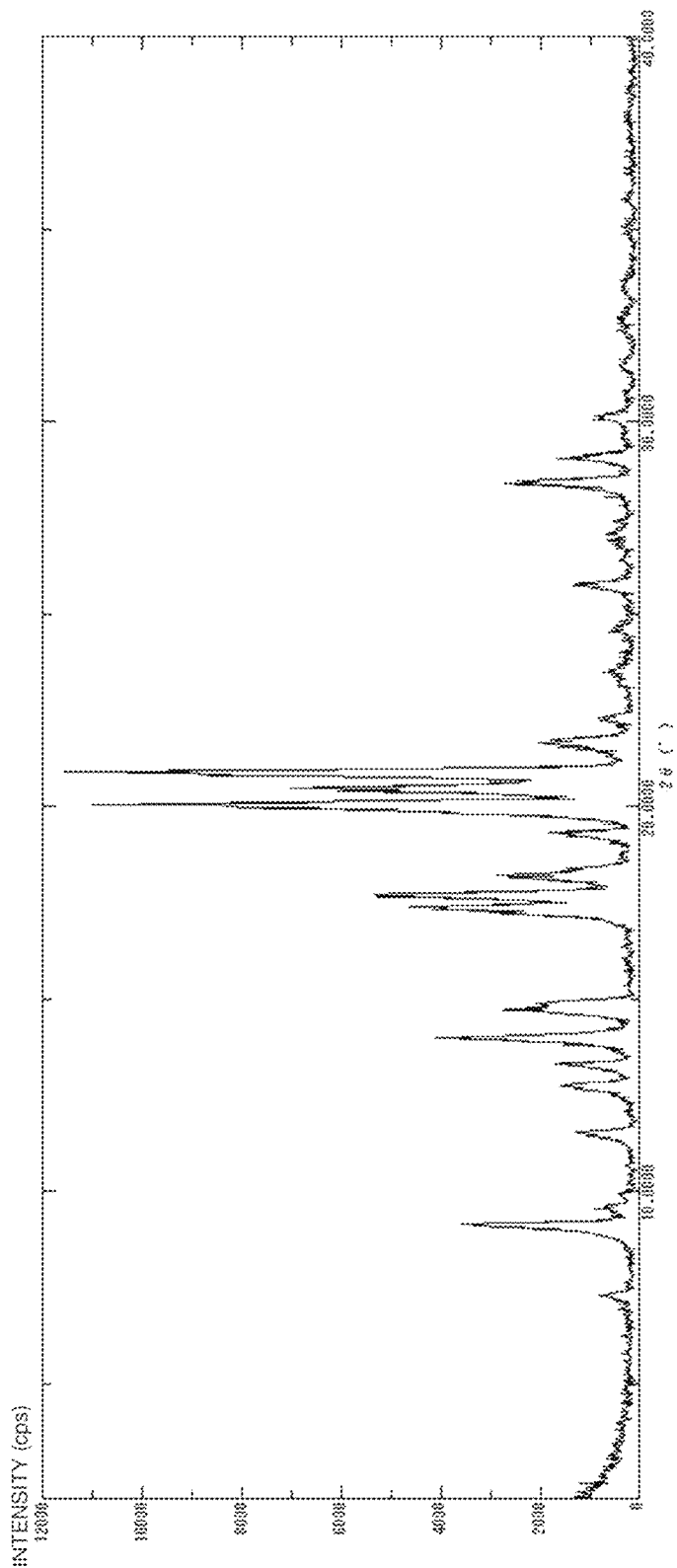

[Figure 3]
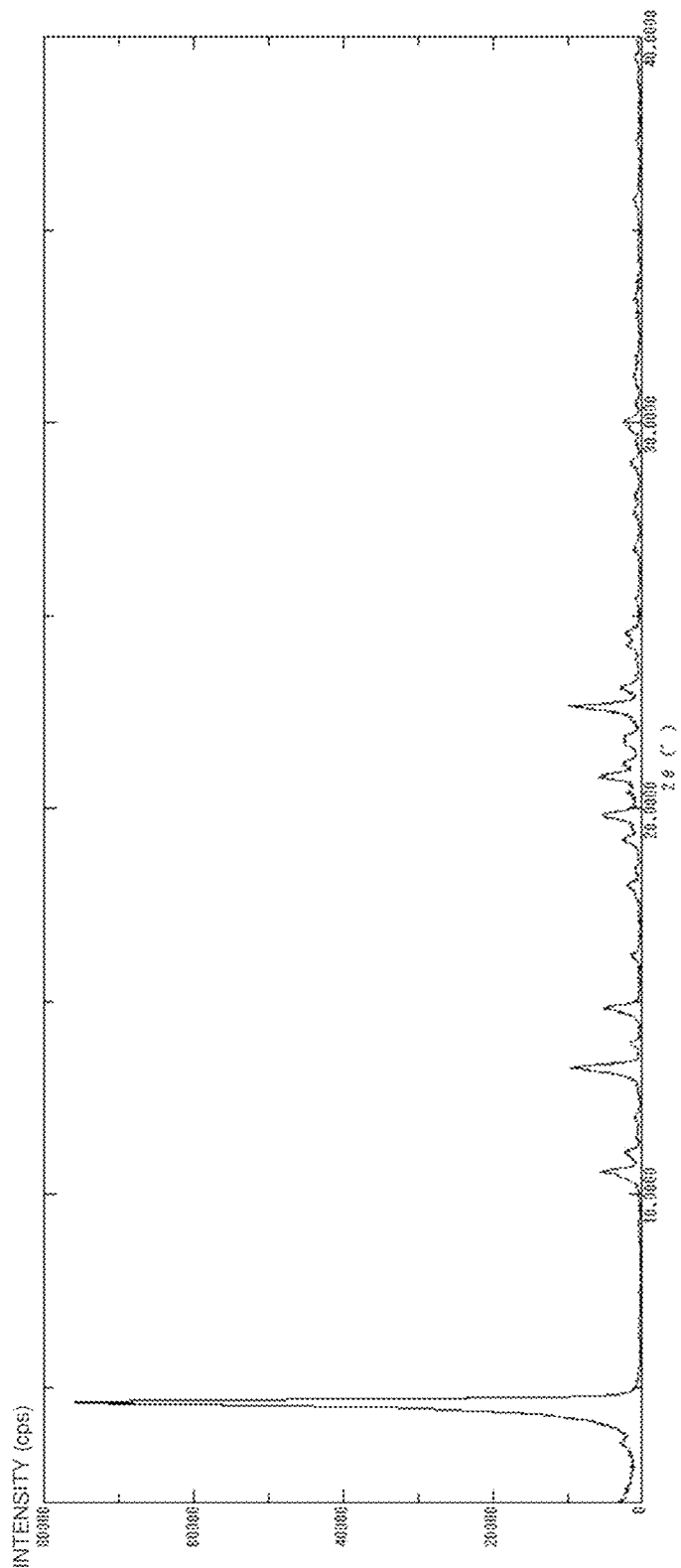

[Figure 4]
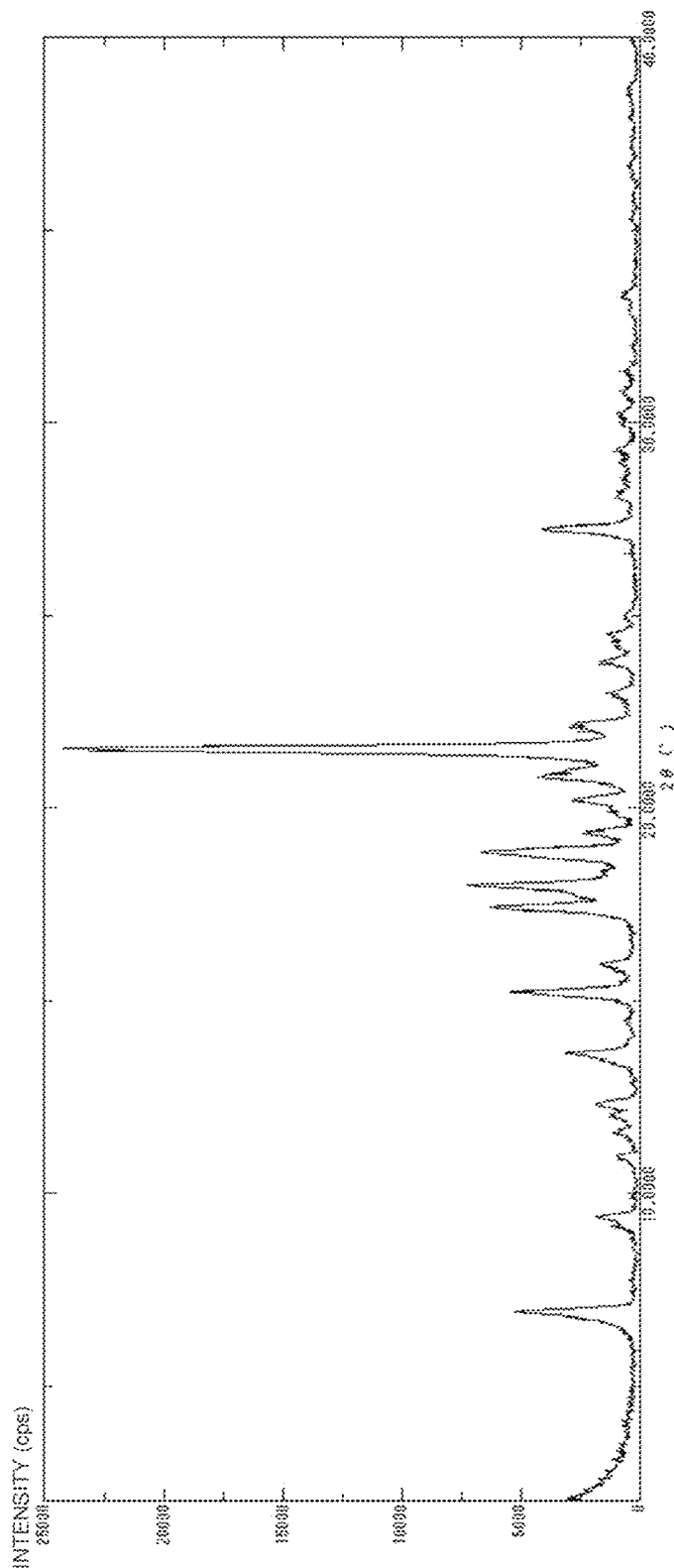

[Figure 5]
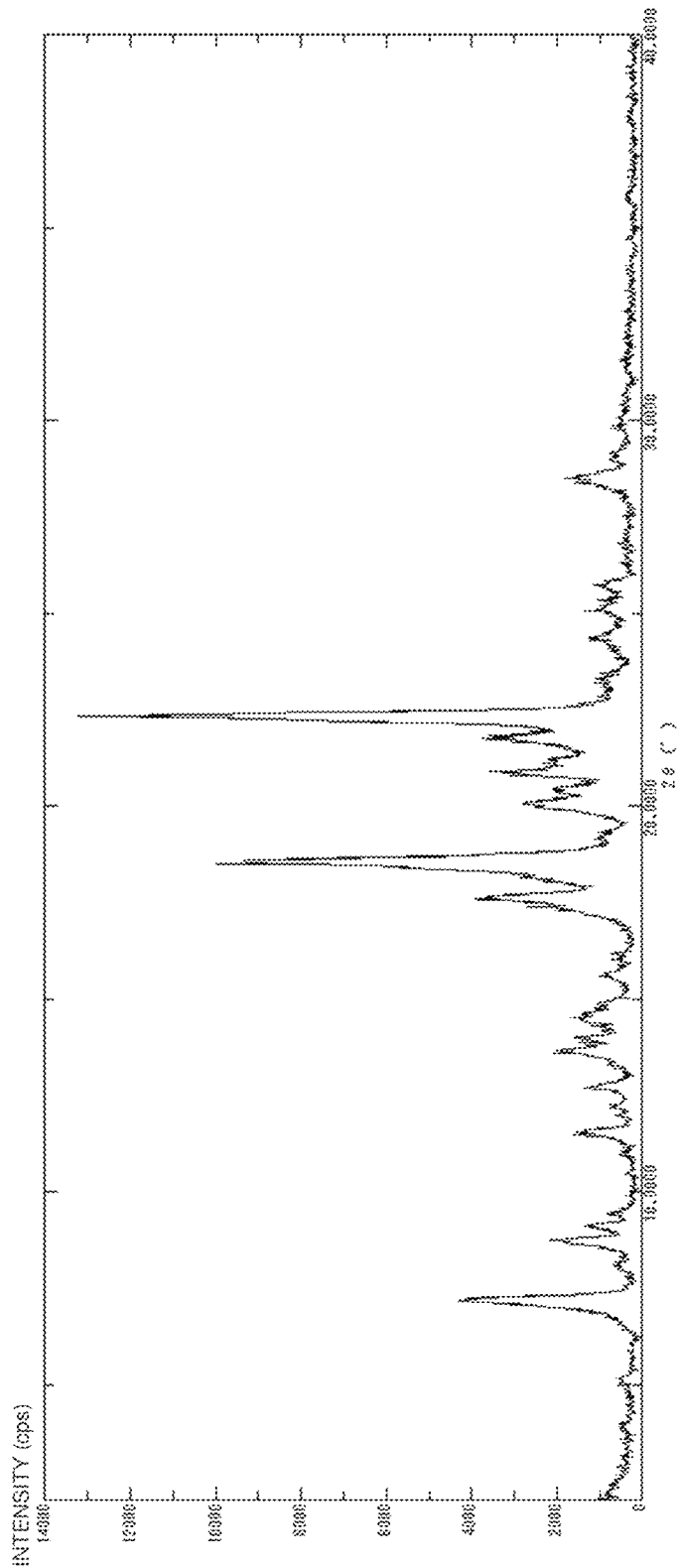

[Figure 6]
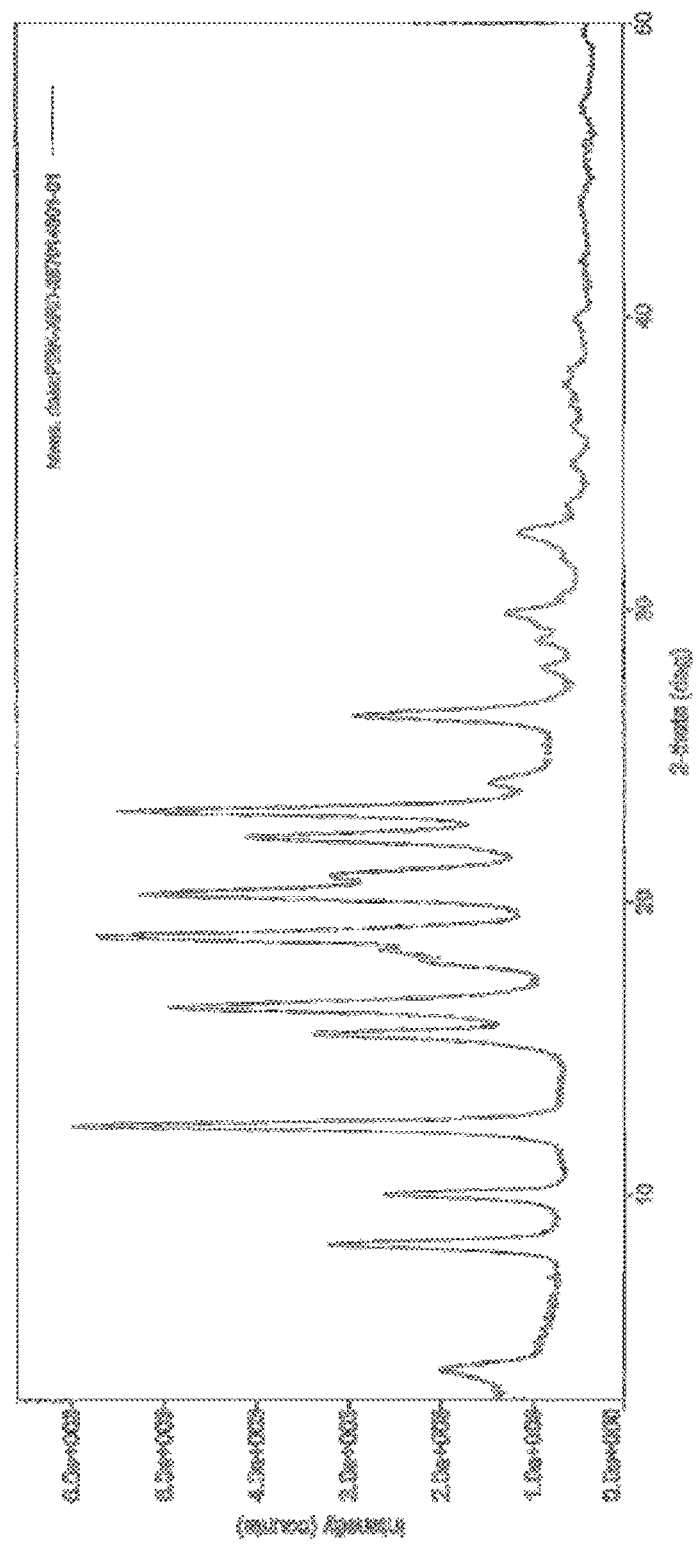

[Figure 7]
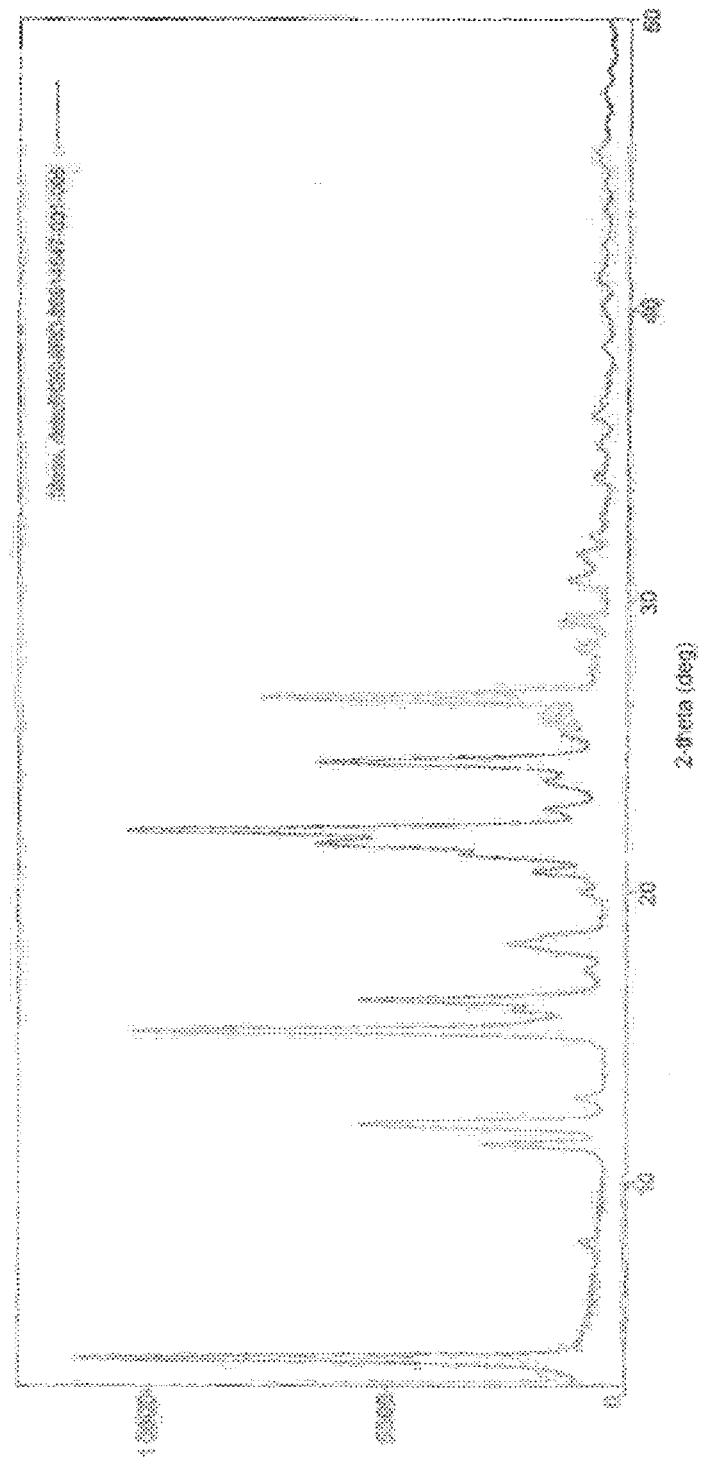

[Figure 8]
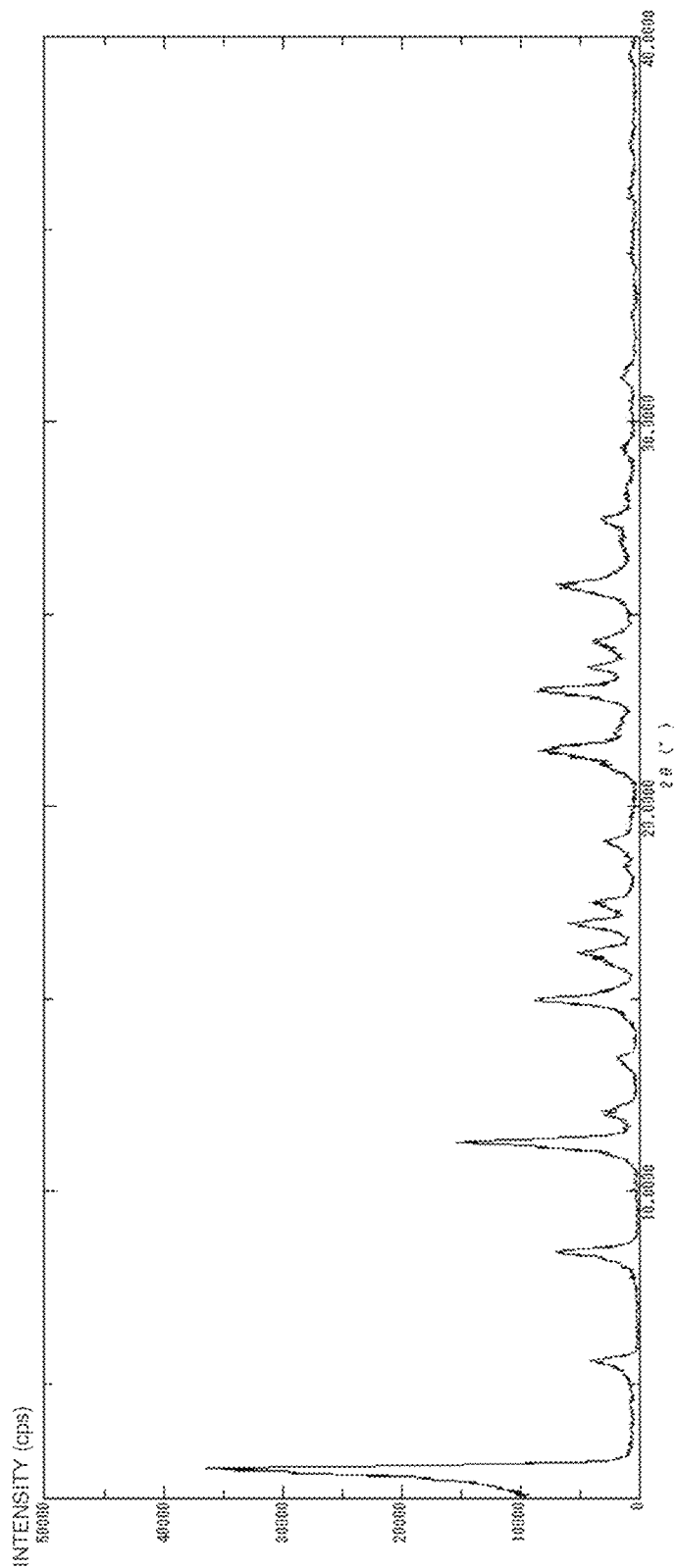

[Figure 9]
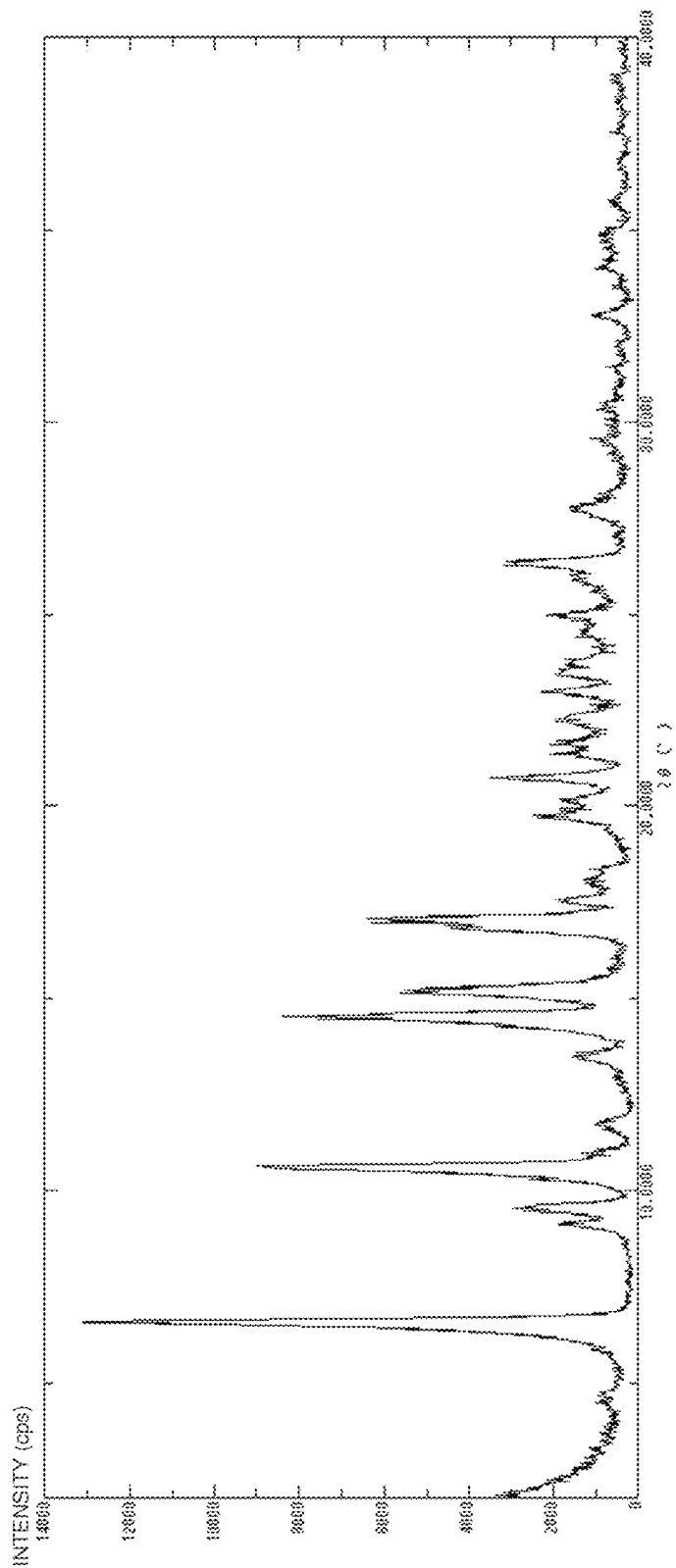

[Figure 10]
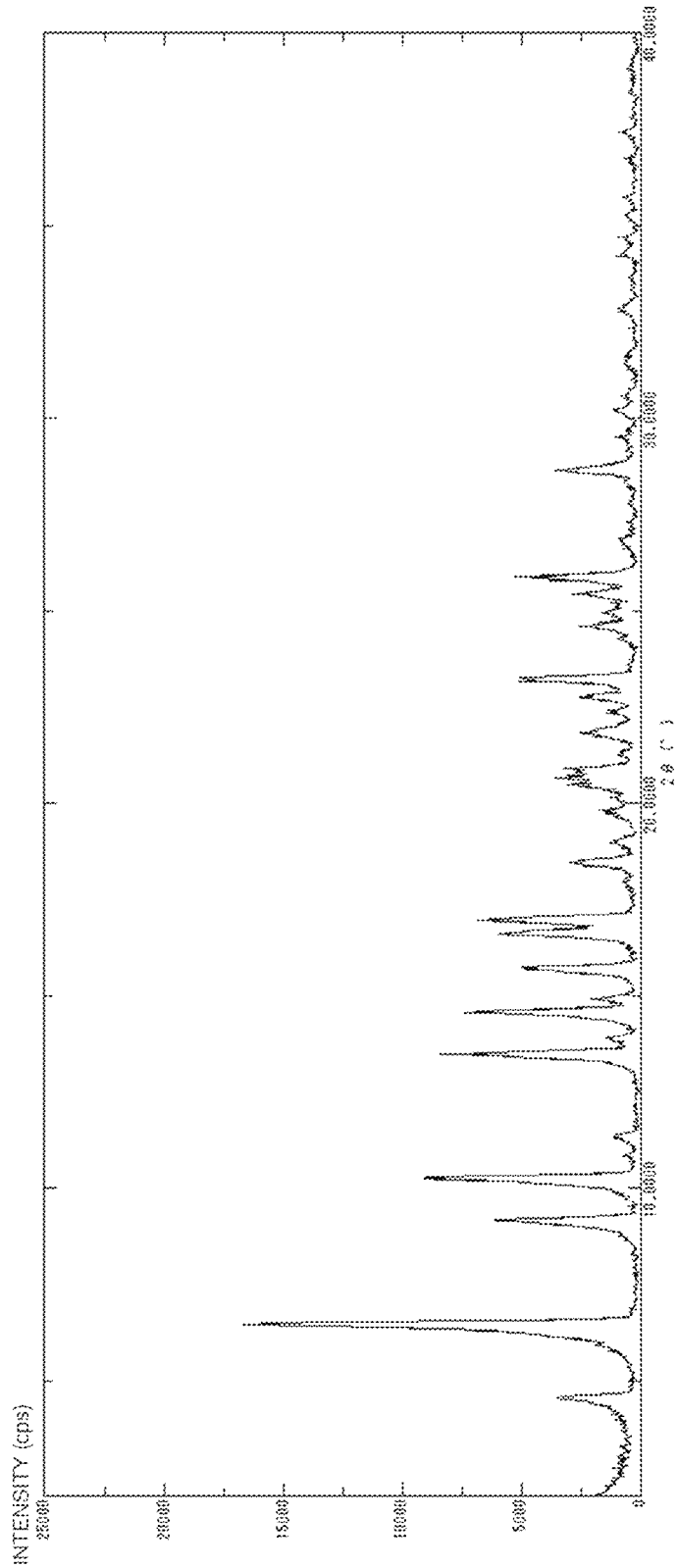

[Figure 11]
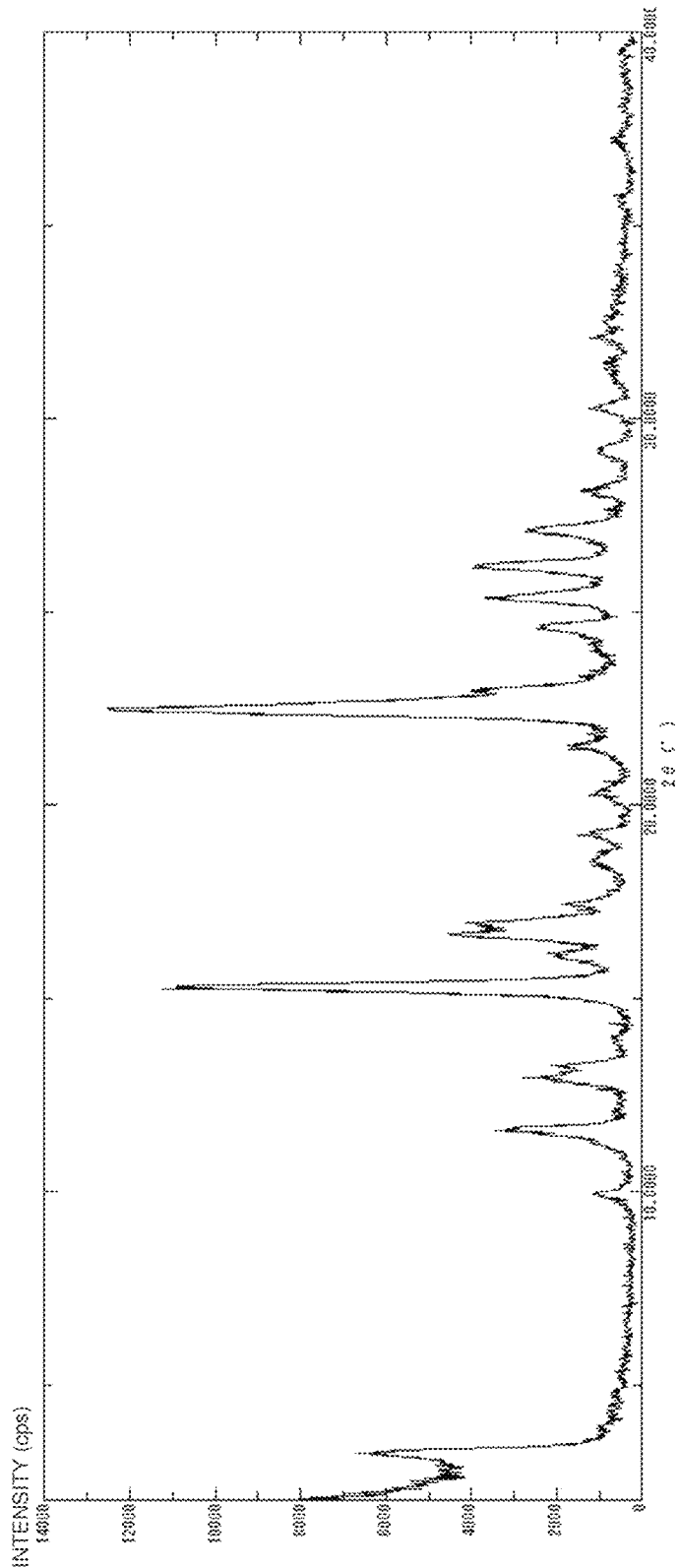

[Figure 12]
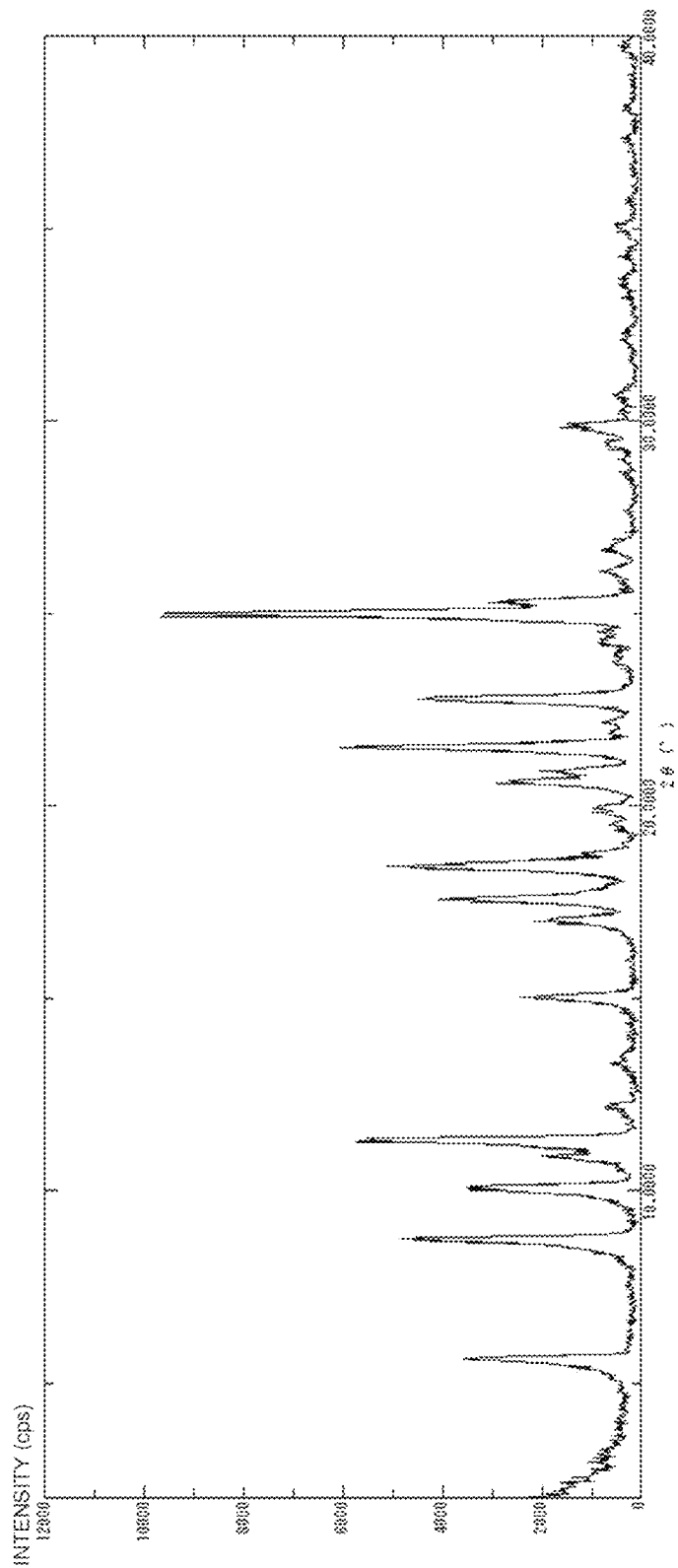

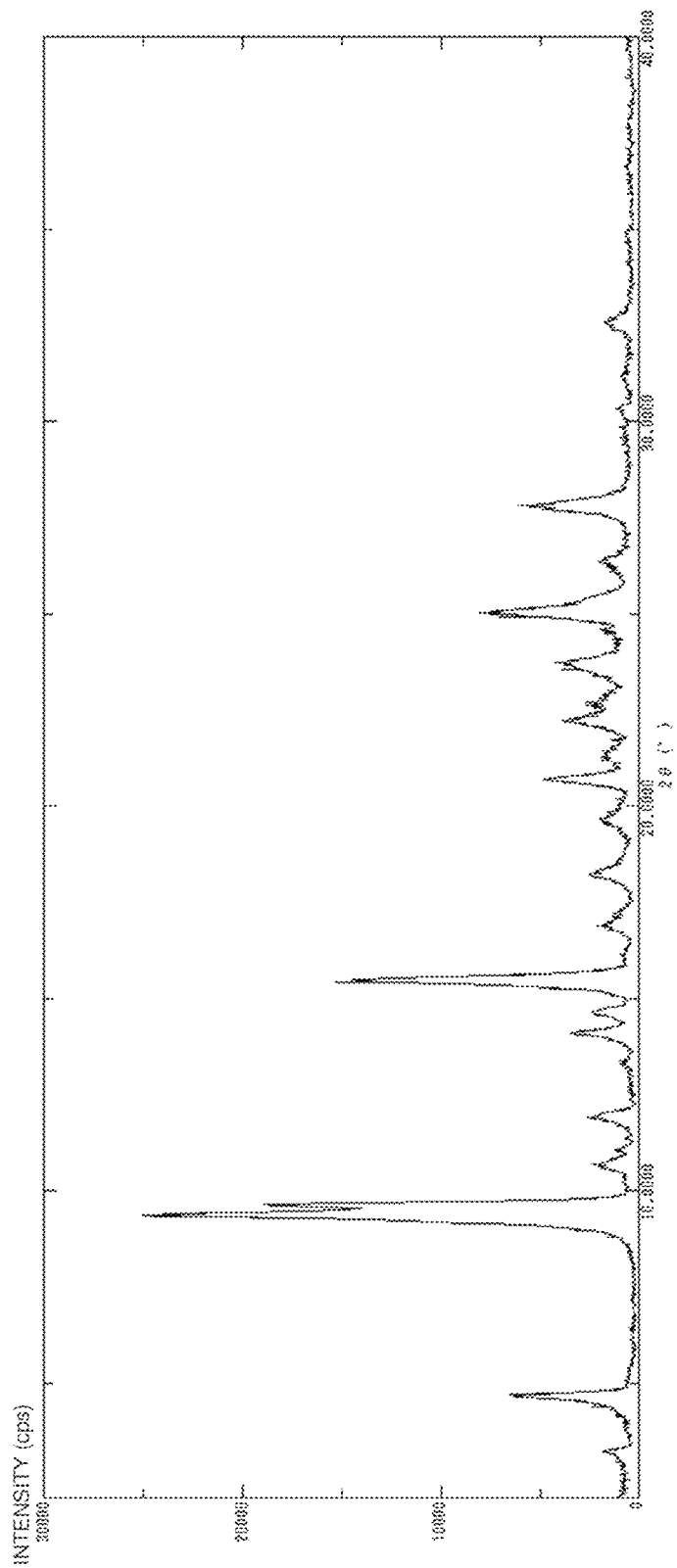
[Figure 13]

[Figure 14]
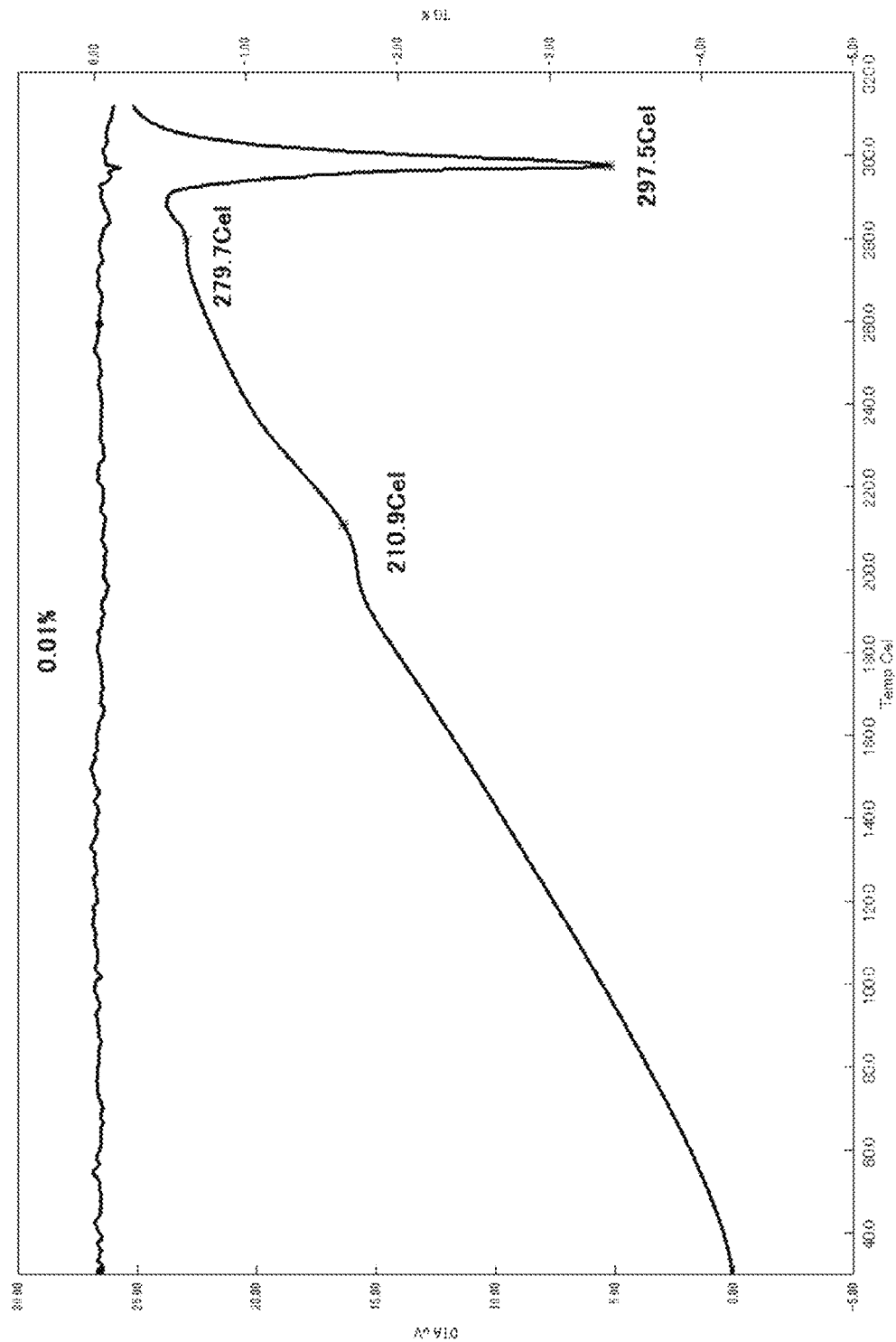

[Figure 15]
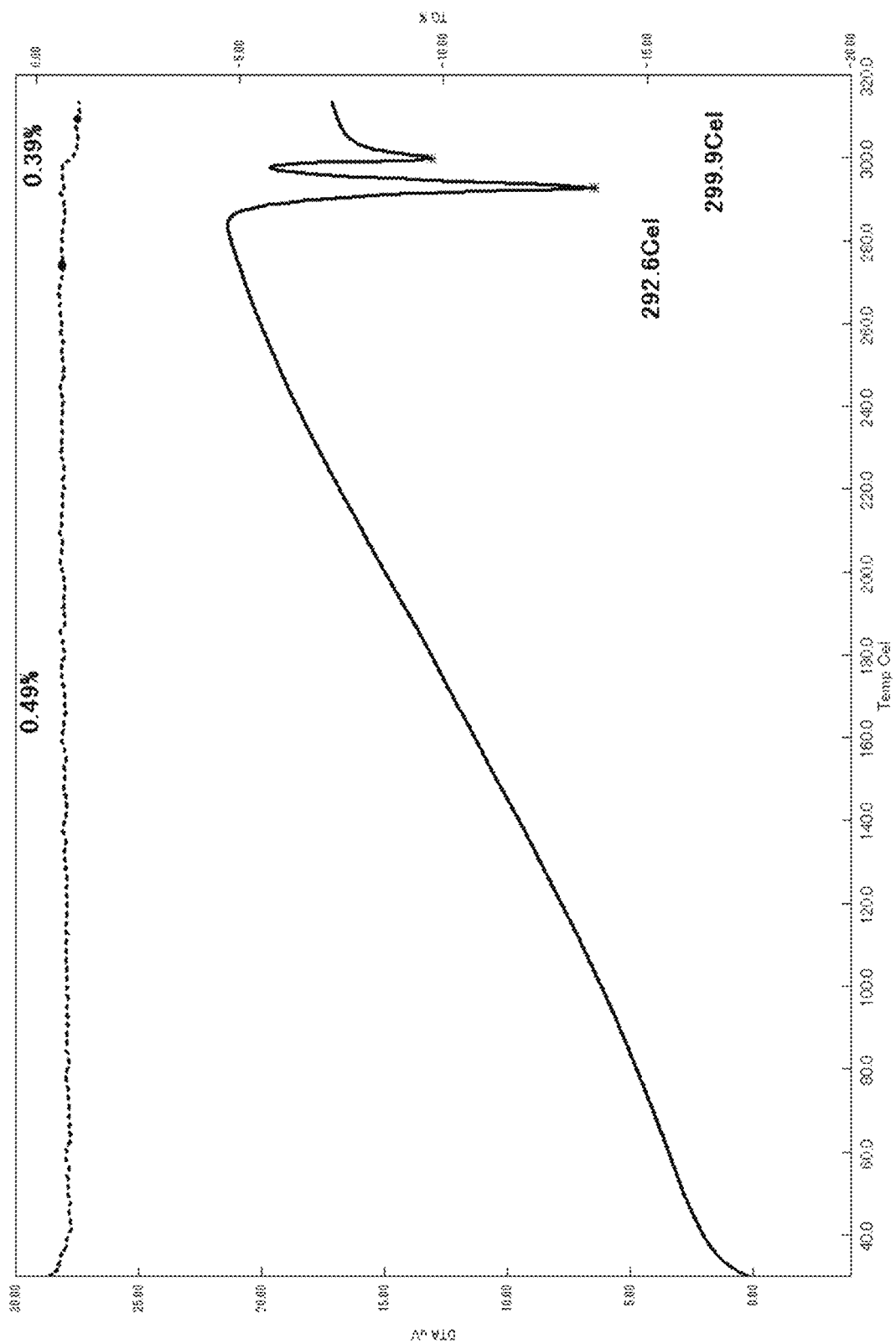

[Figure 16]
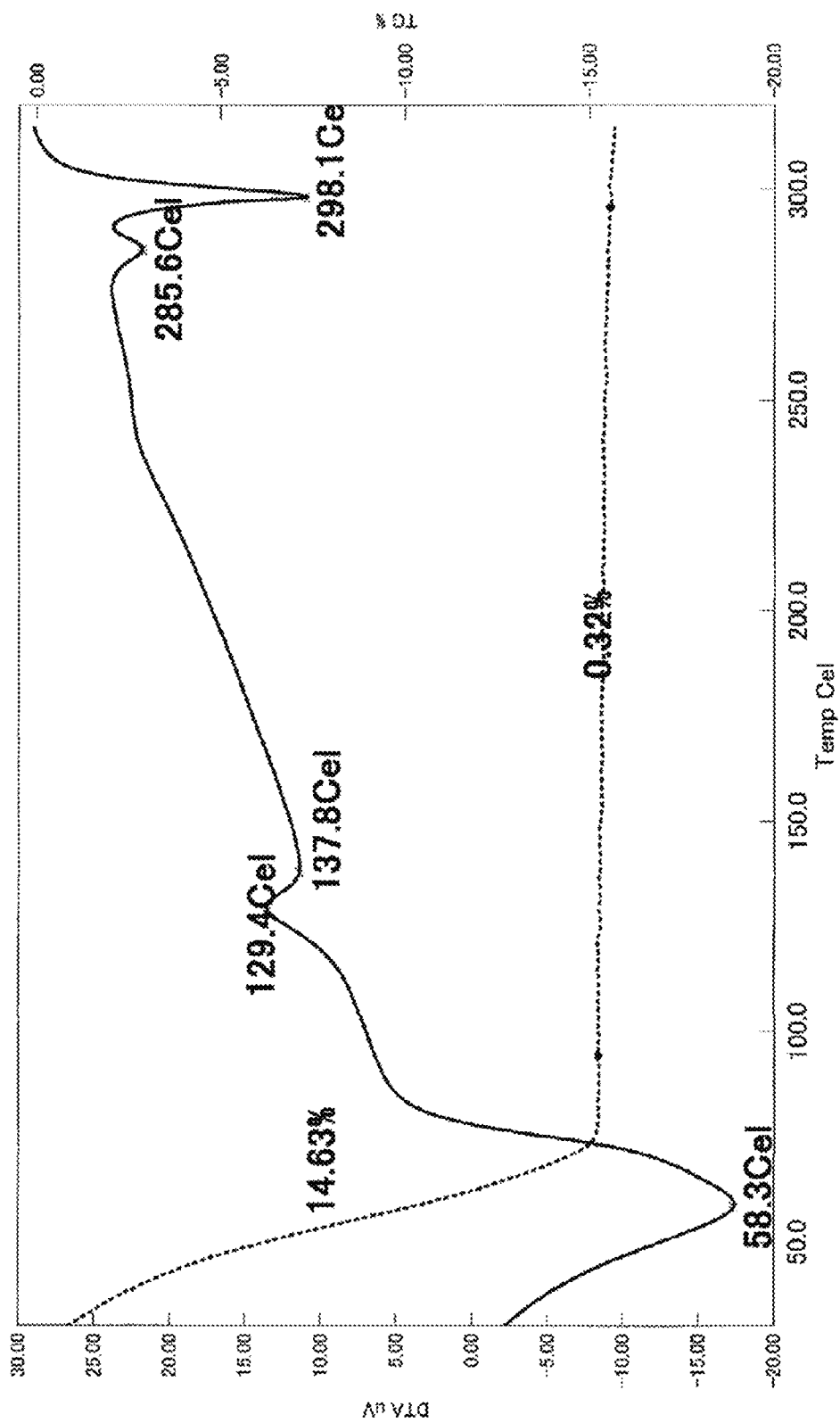

[Figure 17]
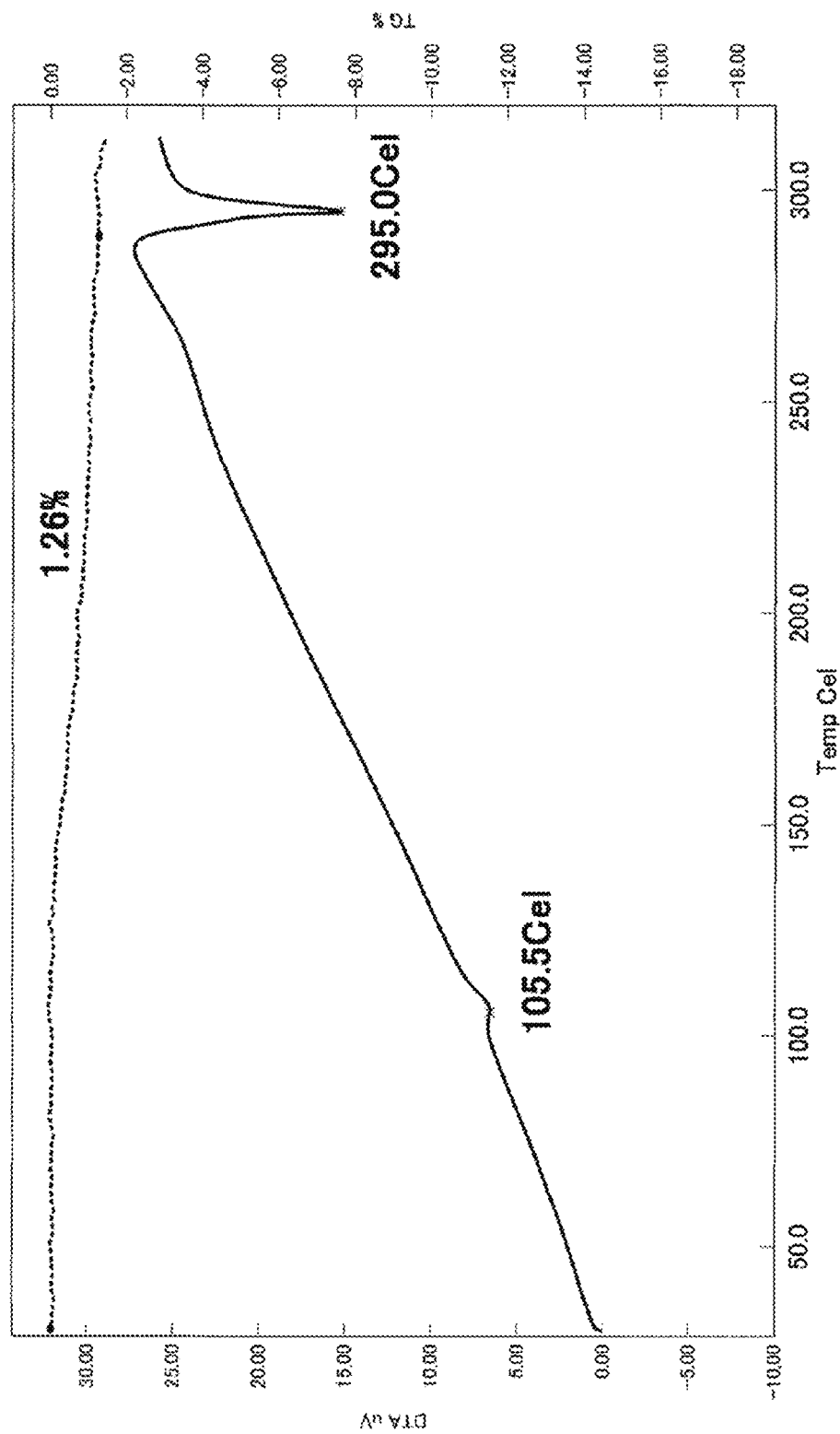

[Figure 18]
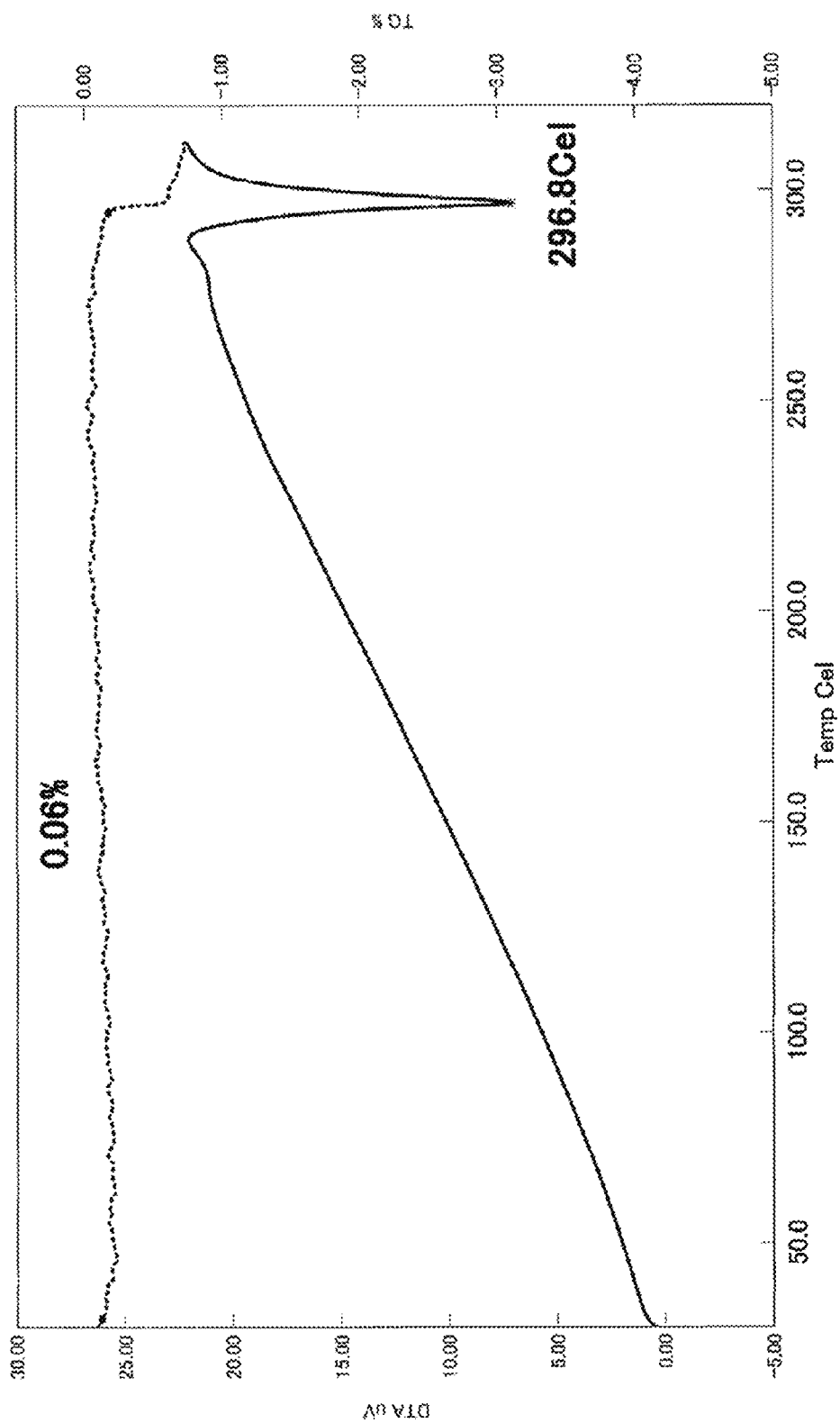

[Figure 19]
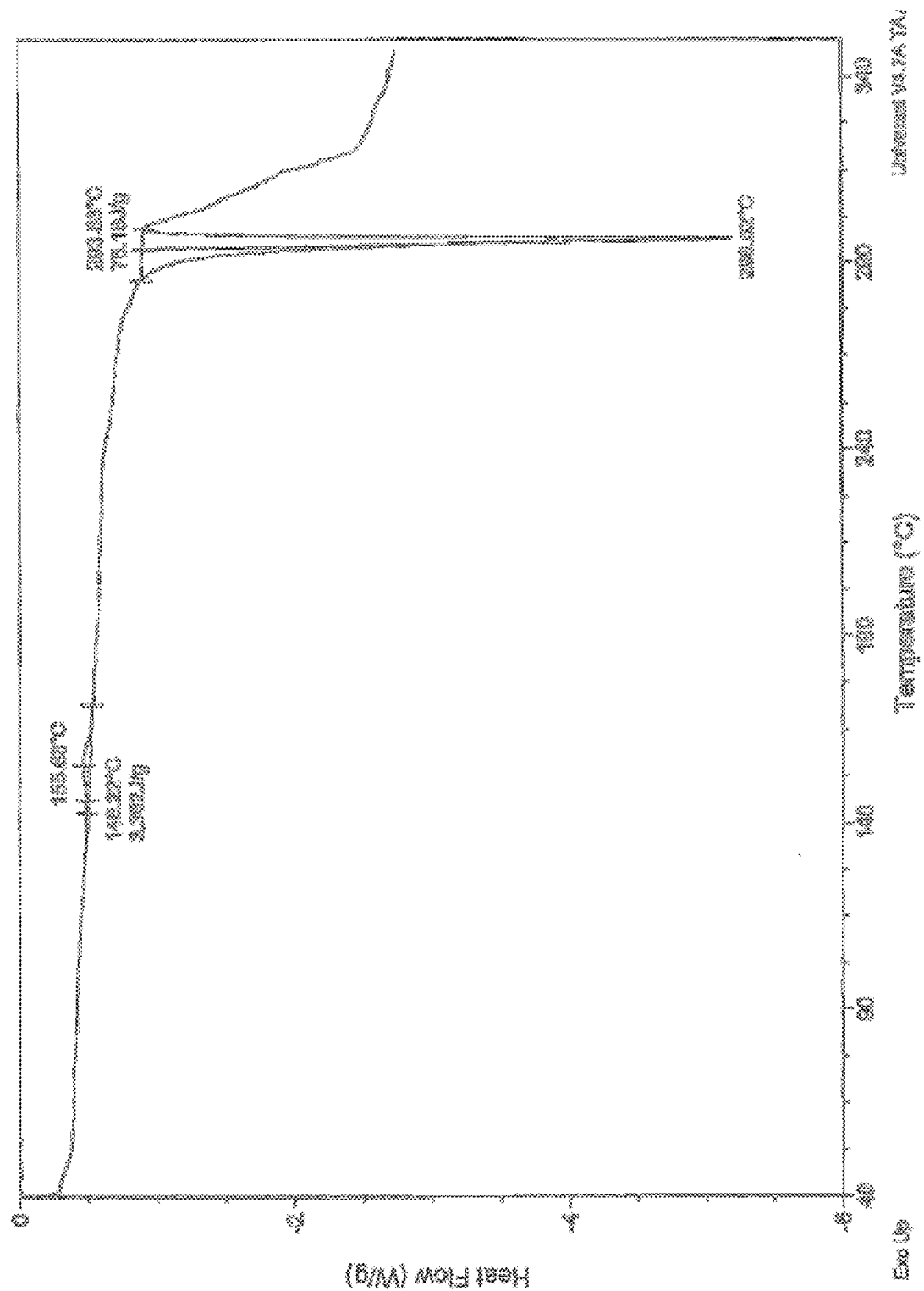

[Figure 20]
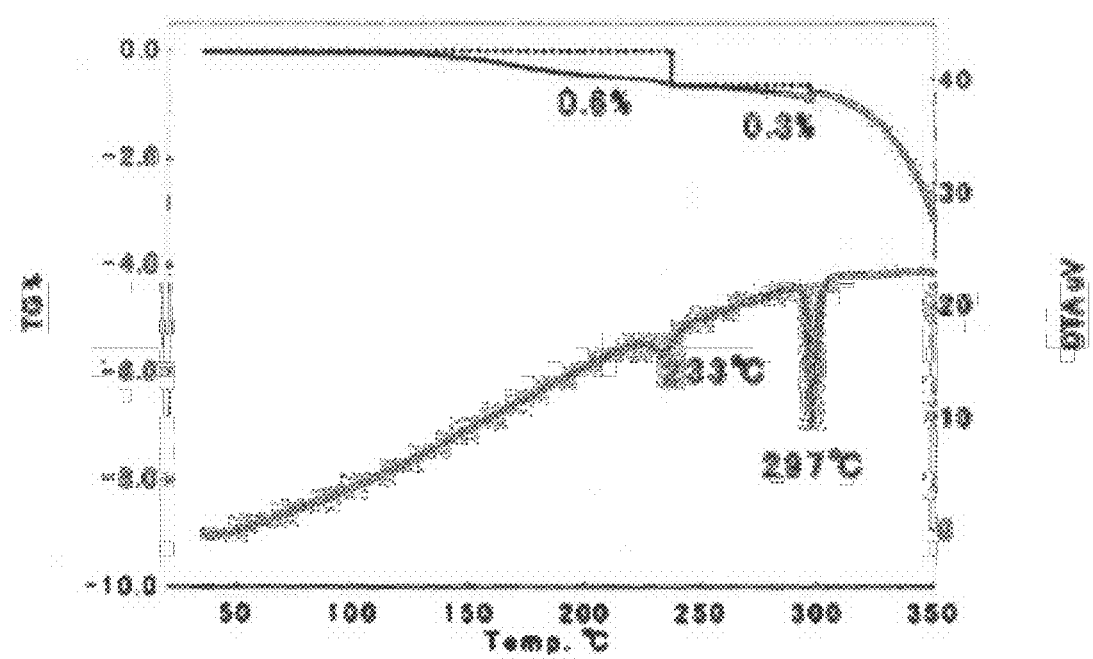

[Figure 21]
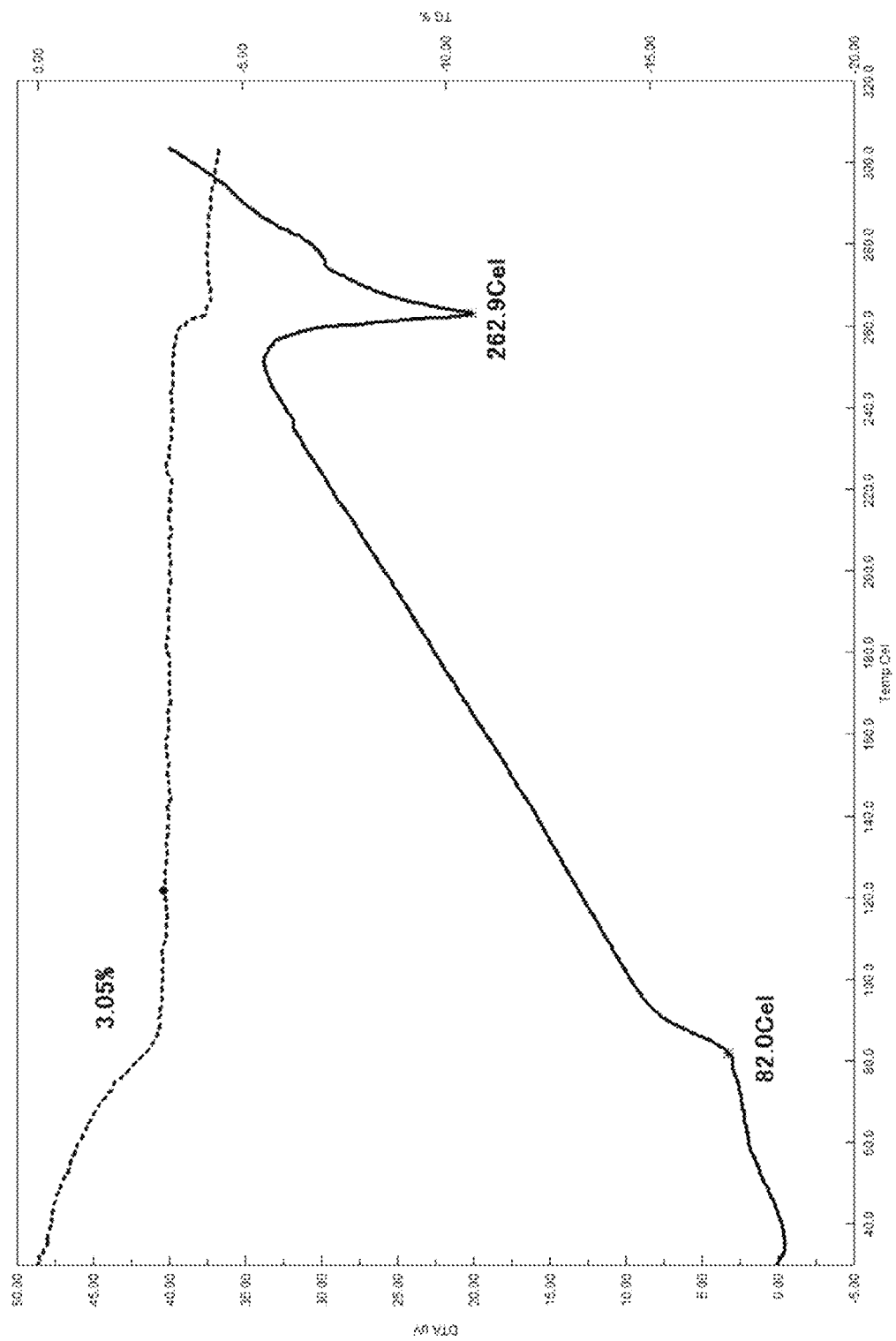

[Figure 22]
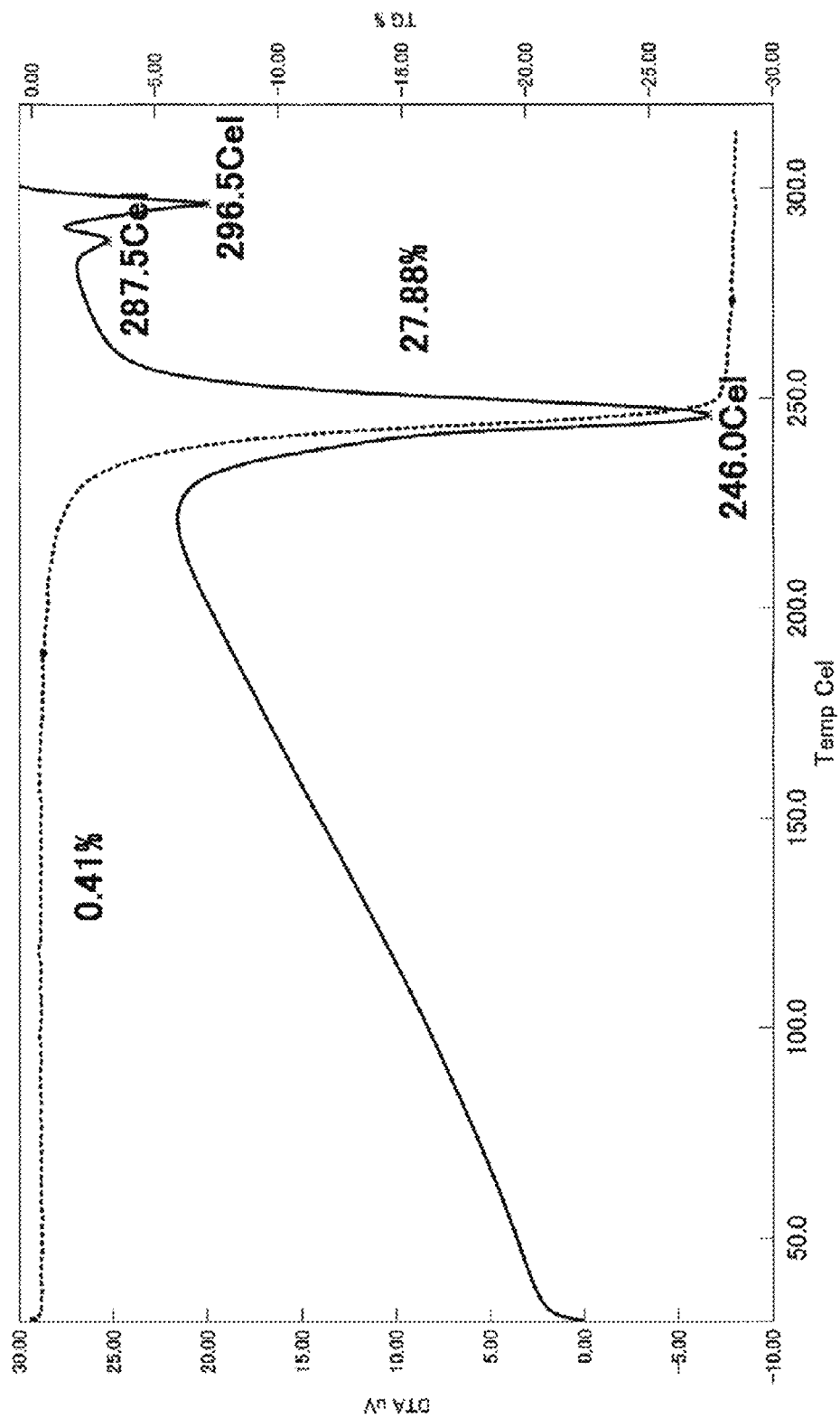

[Figure 23]
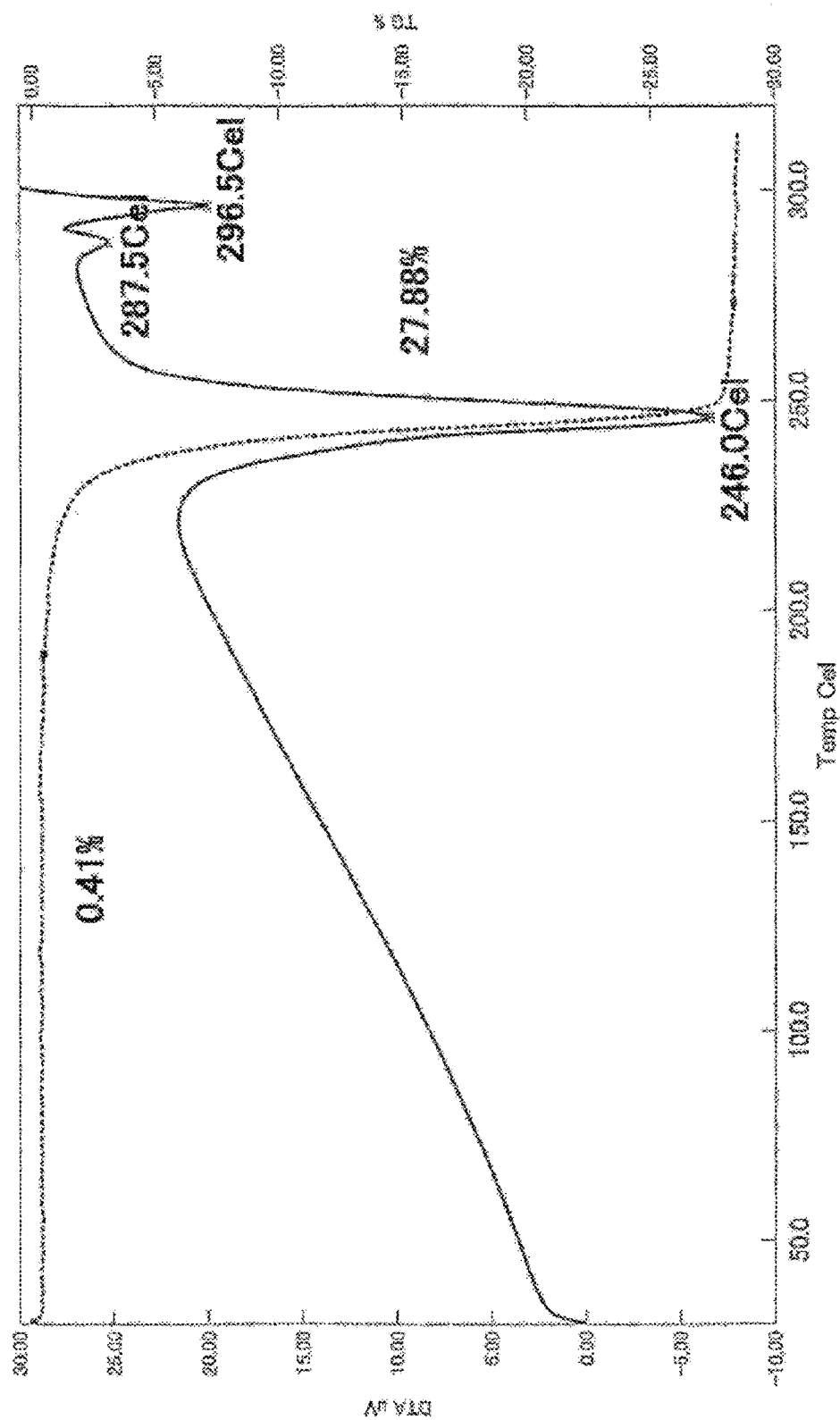

[Figure 24]
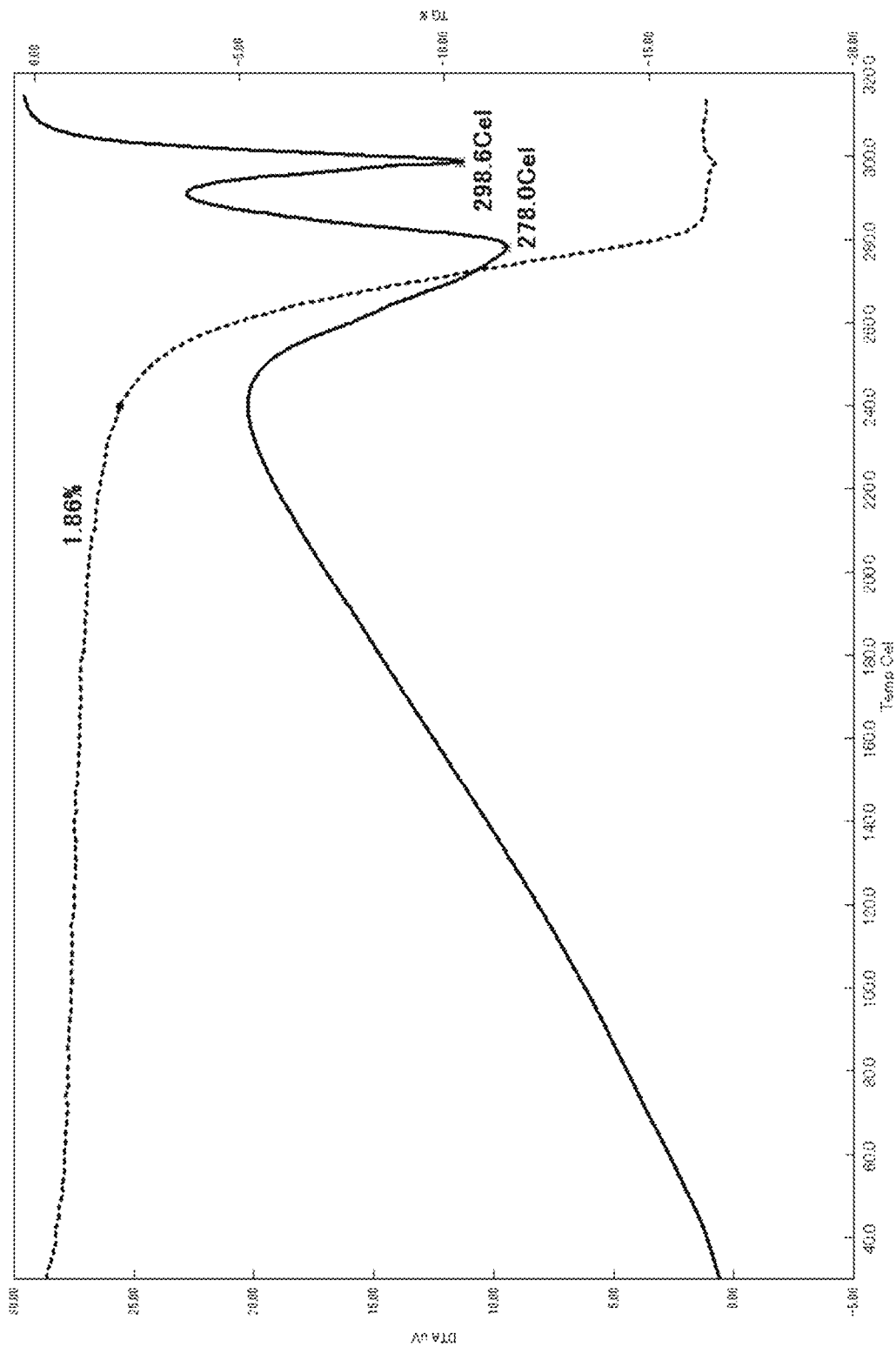

[Figure 25]
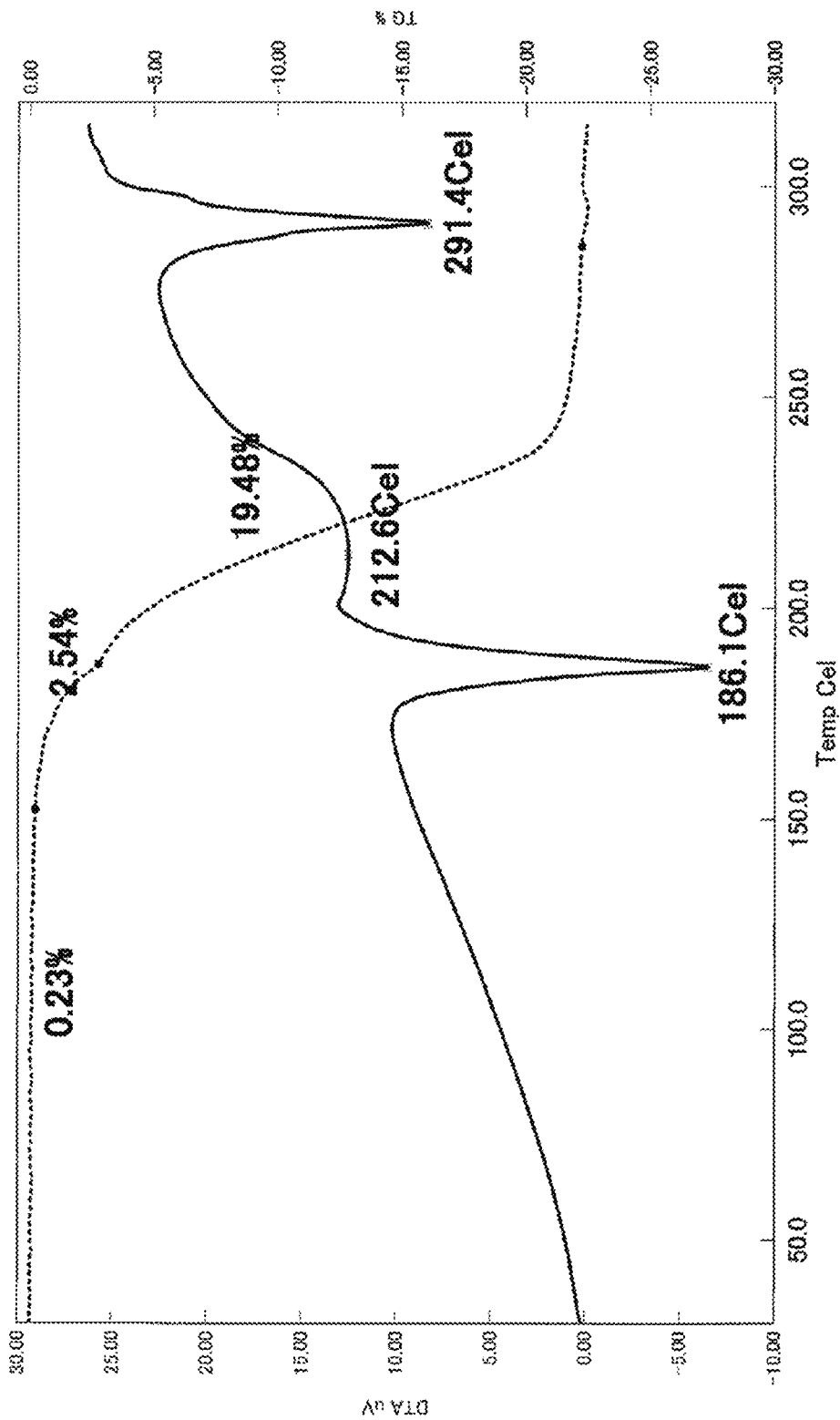

[Figure 26]
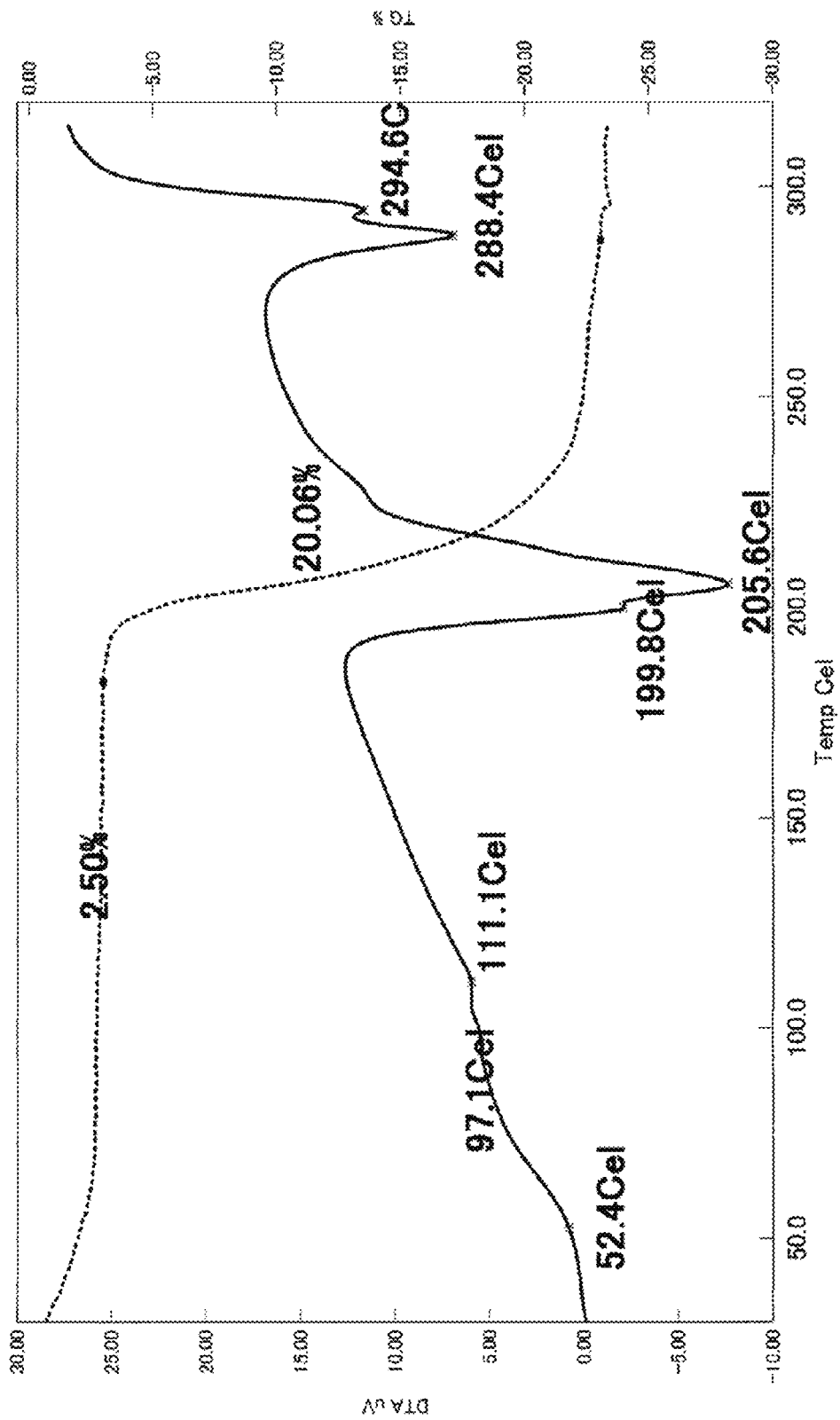

CRYSTALS OF [2-(1-METHYL-1H-PYRAZOL-4-YL)-6(MORPHOLIN-4-YL)-9H-PURIN-8-YL][4-(MORPHOLIN-4-YL)PIPERIDIN-1-YL] METHANONE AND PHARMACEUTICALLY ACCEPTABLE SALT THEREOF

TECHNICAL FIELD

The present invention relates to a crystal of [2-(1-methyl-1H-pyrazol-4-yl)-6-(morpholin-4-yl)-9H-purin-8-yl][4-(morpholin-4-yl)piperidin-1-yl]methanone and a pharmaceutically acceptable salt thereof having advantageous characteristics.

BACKGROUND ART

The phosphatidylinositol 3-kinase (PI3K) family are lipid kinases. The kinases are classified into three classes: class I, class II and class III. The classification is based on structure, regulation and in vitro lipid substrate specificity. Class I PI3Ks, which are most widely studied, are activated by G-protein binding receptors, growth factors and cell surface receptors such as insulin. Class I PI3Ks are further classified into two subclasses: IA and IB. PI3K IA is a heterodimer composed of a catalytic p110 subunit ($\alpha$, $\beta$ or $\delta$) and a regulatory subunit (p85, p55, p50). PI3K IB is a member of PI3K$\gamma$. PI3K$\alpha$ is involved in glucose metabolism and insulin signaling. PI3K$\delta$ and PI3K$\gamma$ are mainly expressed in the hematopoietic system. PI3K$\delta$ is essential for expression and activation of inflammatory mediators, induction of inflammatory cells, airway remodeling and organization of both congenital and adaptive immune response including chronic corticosteroid insensitive airway inflammation. These have been pharmacologically clarified by gene manipulation (Non Patent Literatures 1-3).

PI3Ks have been investigated as targets for developing drugs by various pharmaceutical companies. PI3K$\delta$ inhibitors are described in, e.g., Patent Literatures 1-21; however, a PI3K$\delta$ inhibitor having a pyrazole structure has not yet been disclosed.

Generally, an amorphous-solid drug substance is less stable to environmental conditions such as light, air, humidity and temperature during storage of the drug substance and processing to a drug product or storage of a drug product thereof. The low stability may become a serious problem for pharmaceutical products requiring an extremely high purity. In these circumstances, it has been desired to provide crystals, which often show more advantageous physicochemical properties.

Further, for a compound having crystal polymorphic forms, the physical properties may vary depending on the crystal. Particularly in the field of pharmaceutical products, properties such as solubility, dissolution rate, stability and absorbability are known to vary. Because of this, it is considered that even when the same compound is used, intended potency cannot be obtained in some cases due to a difference in the crystal form; whereas, in other cases, a different potency from expectation is produced, leading to an unexpected situation. For these reasons, it is desirable to provide a compound having the same quality, which is expected to always provide a constant potency.

CITATION LIST

Patent Literatures

Patent Literature 1: WO2012/082997
Patent Literature 2: WO2012/037226
Patent Literature 3: WO2012/007493
Patent Literature 4: WO2012/107465
Patent Literature 5: WO2011/058027
Patent Literature 6: WO2010/136491
Patent Literature 7: WO2010/138589
Patent Literature 8: WO2010/044401
Patent Literature 9: WO2009/146406
Patent Literature 10: WO2009/045174
Patent Literature 11: WO2009/045175
Patent Literature 12: WO2009/053716
Patent Literature 13: GB2431156
Patent Literature 14: WO2012/104776
Patent Literature 15: WO2010/005558
Patent Literature 16: WO2010/114494
Patent Literature 17: WO2009/100406
Patent Literature 18: WO2009/034386
Patent Literature 19: WO2008/116129
Patent Literature 20: WO2005/000404
Patent Literature 21: WO2004/035740

Non Patent Literature

Non Patent Literature 1: Rommel C, et al. Nat. Rev. Immunol. 2007; 7(3): 191-201
Non Patent Literature 2: Medina-Tato D A, et al. Immunology. 2007; 121(4): 448-61
Non Patent Literature 3: Foster J G, et al. Pharmacol. Rev. 2012; 64(4): 1027-54

SUMMARY OF INVENTION

Technical Problem

An object of the present invention is to provide a PI3K$\delta$ inhibitor having a pyrazole derivative skeleton as a therapeutic agent for inflammatory diseases and autoimmune diseases caused by dysregulation of PI3K$\delta$; at the same time, to provide a crystal having excellent characteristics in terms of properties such as storage stability and handling during production of a drug, as a pharmaceutical product or a raw material for a pharmaceutical product.

Solution to Problem

The present inventors conducted intensive studies with a view to attaining these objects. As a result, they found [2-(1-methyl-1H-pyrazol-4-yl)-6-(morpholin-4-yl)-9H-purin-8-yl][4-(morpholin-4-yl)piperidin-1-yl]methanone represented by following formula (I) (hereinafter, also referred to as compound (I)) and a pharmaceutically acceptable salt thereof as a novel PI3K$\delta$ inhibitor, and found a crystal of the compound having excellent characteristics in terms of properties such as storage stability and handling during production of a drug, or as a pharmaceutical product or a raw material for a pharmaceutical product. Based on these findings, the present invention was accomplished.

[Formula 1]

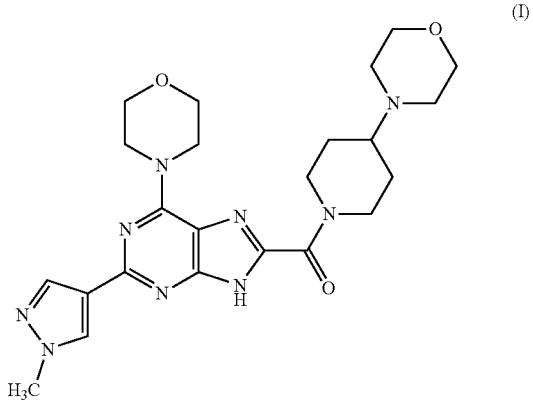

The present invention relates to the following (1) to (29).

(1) A crystal of [2-(1-methyl-1H-pyrazol-4-yl)-6-(morpholin-4-yl)-9H-purin-8-yl][4-(morpholin-4-yl)piperidin-1-yl]methanone.

(2) The crystal according to (1), having at least 5 peaks at diffraction angles (2θ) selected from 3.9±0.2, 11.8±0.2, 15.2±0.2, 15.8±0.2, 21.7±0.2, 22.0±0.2 and 25.3±0.2 in powder X-ray diffraction using CuKα radiation.

(3) The crystal according to (1), having at least 5 peaks at diffraction angles (2θ) selected from 9.1±0.2, 13.9±0.2, 14.7±0.2, 17.4±0.2, 17.6±0.2, 20.0±0.2, 20.4±0.2 and 20.9±0.2 in powder X-ray diffraction using CuKα radiation.

(4) The crystal according to (1), having at least 5 peaks at diffraction angles (2θ) selected from 4.6±0.2, 10.6±0.2, 13.3±0.2, 14.8±0.2, 19.8±0.2, 20.8±0.2 and 22.6±0.2 in powder X-ray diffraction using CuKα radiation.

(5) The crystal according to (1), having at least 5 peaks at diffraction angles (2θ) selected from 6.9±0.2, 15.2±0.2, 17.4±0.2, 18.0±0.2, 18.8±0.2, 20.8±0.2, 21.5±0.2 and 27.2±0.2 in powder X-ray diffraction using CuKα radiation.

(6) The crystal according to (1), having at least 5 peaks at diffraction angles (2θ) selected from 7.2±0.2, 8.7±0.2, 17.6±0.2, 18.5±0.2, 20.0±0.2, 20.9±0.2 and 21.7±0.2 in powder X-ray diffraction using CuKα radiation.

(7) The crystal according to (1), having at least 5 peaks at diffraction angles (2θ) selected from 4.1±0.2, 8.3±0.2, 10.0±0.2, 12.4±0.2, 15.5±0.2, 16.4±0.2, 17.9±0.2 and 18.4±0.2 in powder X-ray diffraction using CuKα radiation.

(8) The crystal according to (1), having at least 5 peaks at diffraction angles (2θ) selected from 3.9±0.2, 12.0±0.2, 15.2±0.2, 16.3±0.2, 21.2±0.2, 21.6±0.2, 22.1±0.2 and 24.4±0.2 in powder X-ray diffraction using CuKα radiation.

(9) A crystal of a p-toluenesulfonic acid salt of [2-(1-methyl-1H-pyrazol-4-yl)-6-(morpholin-4-yl)-9H-purin-8-yl][4-(morpholin-4-yl)piperidin-1-yl]methanone.

(10) The crystal according to (9), having at least 5 peaks at diffraction angles (2θ) selected from 2.8±0.2, 5.6±0.2, 8.4±0.2, 11.2±0.2, 15.0±0.2, 21.4±0.2, 22.9±0.2 and 25.7±0.2 in powder X-ray diffraction using CuKα radiation.

(11) A crystal of a citric acid salt of [2-(1-methyl-1H-pyrazol-4-yl)-6-(morpholin-4-yl)-9H-purin-8-yl][4-(morpholin-4-yl)piperidin-1-yl]methanone.

(12) The crystal according to (11), having at least 6 peaks at diffraction angles (2θ) selected from 6.5±0.2, 9.5±0.2, 10.6±0.2, 14.5±0.2, 15.1±0.2, 17.0±0.2, 20.7±0.2 and 26.3±0.2 in powder X-ray diffraction using CuKα radiation.

(13) The crystal according to (11), having at least 6 peaks at diffraction angles (2θ) selected from 4.5±0.2, 6.4±0.2, 9.1±0.2, 10.2±0.2, 13.5±0.2, 14.5±0.2, 16.9±0.2 and 25.8±0.2 in powder X-ray diffraction using CuKα radiation.

(14) A crystal of an oxalic acid salt of [2-(1-methyl-1H-pyrazol-4-yl)-6-(morpholin-4-yl)-9H-purin-8-yl][4-(morpholin-4-yl)piperidin-1-yl]methanone.

(15) The crystal according to (14), having at least 5 peaks at diffraction angles (2θ) selected from 3.2±0.2, 11.6±0.2, 15.2±0.2, 16.6±0.2, 16.9±0.2, 22.5±0.2, 25.3±0.2 and 26.1±0.2 in powder X-ray diffraction using CuKα radiation.

(16) A crystal of a glutaric acid salt of [2-(1-methyl-1H-pyrazol-4-yl)-6-(morpholin-4-yl)-9H-purin-8-yl][4-(morpholin-4-yl)piperidin-1-yl]methanone.

(17) The crystal according to (16), having at least 5 peaks at diffraction angles (2θ) selected from 5.6±0.2, 8.7±0.2, 11.2±0.2, 17.5±0.2, 18.4±0.2, 21.5±0.2, 22.7±0.2 and 24.9±0.2 in powder X-ray diffraction using CuKα radiation.

(18) A crystal of a malic acid salt of [2-(1-methyl-1H-pyrazol-4-yl)-6-(morpholin-4-yl)-9H-purin-8-yl][4-(morpholin-4-yl)piperidin-1-yl]methanone.

(19) The crystal according to (18), having at least 5 peaks at diffraction angles (2θ) selected from 4.6±0.2, 9.3±0.2, 9.6±0.2, 14.1±0.2, 15.4±0.2, 20.6±0.2, 25.0±0.2 and 27.8±0.2 in powder X-ray diffraction using CuKα radiation.

(20) A pharmaceutical composition containing the crystal according to any one of (1) to (19) as an active ingredient.

(21) The pharmaceutical composition according to (20), for use for psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

(22) A phosphatidylinositol 3-kinase δ (PI3Kδ) inhibitor containing the crystal according to any one of (1) to (19) as an active ingredient.

(23) The inhibitor according to (22), for use for psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

(24) A treatment method for a disease that can be treated by inhibiting PI3Kδ, wherein the crystal according to any one of (1) to (19) is administered.

(25) The treatment method according to (24), wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

(26) The crystal according to any one of (1) to (19) for use in treating a disease that can be treated by inhibiting PI3Kδ.

(27) The crystal according to (26), wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

(28) Use of the crystal according to any one of (1) to (19) for producing a pharmaceutical composition for treating a disease that can be treated by inhibiting PI3Kδ.

(29) The use according to (28), wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

In the present invention, a crystal refers to a solid substance having an internal structure composed of threedimensional highly-ordered repeats of constituent atoms or molecules, and is distinguished from amorphous solid substances or amorphous substances having no such highly-ordered interior structure.

In the present invention, examples of the crystal include a crystal of a compound (I), a crystal of a hydrate of a compound (I), a crystal of a solvate of a compound (I), a crystal of a pharmaceutically acceptable salt of a compound (I), a crystal of a hydrate of a pharmaceutically acceptable salt of a compound (I) and a crystal of a solvate of a pharmaceutically acceptable salt of a compound (I).

In the present invention, it can be confirmed that the compound (I) and a pharmaceutically acceptable salt thereof have a crystalline form by observation under a polarizing microscope, powder X-ray crystal analysis or by using single-crystal X-ray diffraction measurement. Further, the type of crystal can be specified by comparing the characteristics of a crystal based on data of individual indexes measured in advance. Thus, according to a preferable aspect of the present invention, the crystal of the present invention refers to one which can be confirmed as a crystal by using such measuring means.

In the present invention, not only a crystal whose diffraction angle in powder X-ray diffraction is completely identical (with the crystal of the present invention) but also a crystal whose diffraction angle is identical (with the crystal of the present invention) within the range of ±0.2, is included in the present invention. This is customarily carried out, because peak values intrinsically vary, generally due to differences in measuring instruments, samples and sample preparations. This is because since the diffraction angle (2θ) in powder X-ray diffraction may have an error within the range of ±0.2, the value representing the above diffraction angle should be understood to include numerical values within the range of about ±0.2. In powder X-ray diffraction measurement, even if the same crystals are measured, relative intensities thereof are not always identical to each other due to measurement errors of the machine used for measurement and the state of the measurement sample, and the peak intensity may vary depending on the differences (crystal habit) of e.g., crystal particle size and growth face, and the like. Accordingly, if the present invention is expressed based on data of powder X-ray diffraction, not only a crystal whose diffraction angles and relative intensities are identical to those of the crystal described in the specification but also crystals having identical diffraction angles to the crystal described in the specification even if the relative intensities differ therefrom fall within the scope of the present invention.

The novel crystals of [2-(1-methyl-1H-pyrazol-4-yl)-6-(morpholin-4-yl)-9H-purin-8-yl][4-(morpholin-4-yl)piperidin-1-yl]methanone of the present invention and a pharmaceutically acceptable salt thereof (hereinafter, sometimes individually referred to as "the crystal of Example 1 of the present invention", "the crystal of Example 2 of the present invention", "the crystal of Example 3 of the present invention", "the crystal of Example 4 of the present invention", "the crystal of Example 5 of the present invention", "the crystal of Example 6 of the present invention", "the crystal of Example 7 of the present invention", "the crystal of Example 8 of the present invention", "the crystal of Example 9 of the present invention", "the crystal of Example 10 of the present invention", "the crystal of Example 11 of the present invention", "the crystal of Example 12 of the present invention" and "the crystal of Example 13 of the present invention") can be stably supplied as a crystal of a drug substance for use in the production of a medicine and are excellent in hygroscopicity or stability. Differences in these crystal forms are determined particularly by powder X-ray diffraction.

More specifically, the crystal of Example 1 of the present invention is determined as one having peaks in powder X-ray diffraction at angles of 2θ (°) 3.9±0.2, 7.8±0.2, 11.8±0.2, 15.2±0.2, 15.8±0.2, 21.7±0.2, 22.0±0.2, and 25.3±0.2.

More specifically, the crystal of Example 2 of the present invention is determined as one having peaks in powder X-ray diffraction at angles of 2θ (°) 9.1±0.2, 13.9±0.2, 14.7±0.2, 17.4±0.2, 17.6±0.2, 20.0±0.2, 20.4±0.2, and 20.9±0.2.

More specifically, the crystal of Example 3 of the present invention is determined as one having peaks in powder X-ray diffraction at angles of 2θ (°) 4.6±0.2, 10.6±0.2, 13.3±0.2, 14.8±0.2, 19.8±0.2, 20.8±0.2, and 22.6±0.2.

More specifically, the crystal of Example 4 of the present invention is determined as one having peaks in powder X-ray diffraction at angles of 2θ (°) 6.9±0.2, 15.2±0.2, 17.4±0.2, 18.0±0.2, 18.8±0.2, 20.8±0.2, 21.5±0.2, and 27.2±0.2.

More specifically, the crystal of Example 5 of the present invention is determined as one having peaks in powder X-ray diffraction at angles of 2θ (°) 7.2±0.2, 8.7±0.2, 17.6±0.2, 18.5±0.2, 20.0±0.2, 20.9±0.2 and 21.7±0.2.

More specifically, the crystal of Example 6 of the present invention is determined as one having peaks in powder X-ray diffraction at angles of 2θ (°) 4.1±0.2, 8.3±0.2, 10.0±0.2, 12.4±0.2, 15.5±0.2, 16.4±0.2, 17.9±0.2 and 18.4±0.2.

More specifically, the crystal of Example 7 of the present invention is determined as one having peaks in powder X-ray diffraction at angles of 2θ (°) 3.9±0.2, 12.0±0.2, 15.2±0.2, 16.3±0.2, 21.2±0.2, 21.6±0.2, 22.1±0.2, and 24.4±0.2.

More specifically, the crystal of Example 8 of the present invention is determined as one having peaks in powder X-ray diffraction at angles of 2θ (°) 2.8±0.2, 5.6±0.2, 8.4±0.2, 11.2±0.2, 15.0±0.2, 21.4±0.2, 22.9±0.2, and 25.7±0.2.

More specifically, the crystal of Example 9 of the present invention is determined as one having peaks in powder X-ray diffraction at angles of 2θ (°) 6.5±0.2, 9.5±0.2, 10.6±0.2, 14.5±0.2, 15.1±0.2, 17.0±0.2, 20.7±0.2, and 26.3±0.2.

More specifically, the crystal of Example 10 of the present invention is determined as one having peaks in powder X-ray diffraction at angles of 2θ (°) 4.5±0.2, 6.4±0.2, 9.1±0.2, 10.2±0.2, 13.5±0.2, 14.5±0.2, 16.9±0.2, and 25.8±0.2.

More specifically, the crystal of Example 11 of the present invention is determined as one having peaks in powder X-ray diffraction at angles of 2θ (°) 3.2±0.2, 11.6±0.2, 15.2±0.2, 16.6±0.2, 16.9±0.2, 22.5±0.2, 25.3±0.2, and 26.1±0.2.

More specifically, the crystal of Example 12 of the present invention is determined as one having peaks in powder X-ray diffraction at angles of 2θ (°) 5.6±0.2, 8.7±0.2, 11.2±0.2, 17.5±0.2, 18.4±0.2, 21.5±0.2, 22.7±0.2, and 24.9±0.2.

More specifically, the crystal of Example 13 of the present invention is determined as one having peaks in powder X-ray diffraction at angles of 2θ (°) 4.6±0.2, 9.3±0.2, 9.6±0.2, 14.1±0.2, 15.4±0.2, 20.6±0.2, 25.0±0.2, and 27.8±0.2.

Advantageous Effects of Invention

The crystal of [2-(1-methyl-1H-pyrazol-4-yl)-6-(morpholin-4-yl)-9H-purin-8-yl][4-(morpholin-4-yl)piperidin-1-yl]methanone and a pharmaceutically acceptable salt thereof provided by the present invention are excellent in storage stability and suitable for mass synthesis in industrial production, and have satisfactory physical properties as a drug substance of a pharmaceutical product.

DESCRIPTION OF EMBODIMENTS

Now, the present invention will be more specifically described, below.

Another aspect of the present invention relates to a pharmaceutical composition containing a crystal of the present invention as an active ingredient.

The pharmaceutical composition containing a crystal of the invention according to the present application as an active ingredient is preferably provided in the form of a pharmaceutical composition containing a crystal of the present invention and one or two or more pharmaceutically acceptable additives.

Administration may be either in the form of oral administration using tablets, pills, capsules, granules, powders, liquids and solutions and the like or parenteral administration using as injections for intraarticular, intravenous and intramuscular injections, suppositories, eye drops, eye ointments, transdermal liquids and solutions, ointments, transdermal patches, transmucosal liquids and solutions, transmucosal patches and inhalants.

As a solid preparation for oral administration, tablets, powders, granules, capsules, pills or lozenges are mentioned. These solid preparations may contain a crystal of the present invention together with pharmaceutically acceptable additives. Examples of the additives include fillers, extending agents, binders, disintegrants, dissolution accelerators, wetting agents and lubricants. These can be selected as necessary and mixed for producing drugs.

For example, in the case of a tablet, the content of a binder in a pharmaceutical composition is usually, 1 to 10 parts by weight (preferably, 2 to 5 parts by weight); the content of a disintegrant is usually 1 to 40 parts by weight (preferably, 5 to 30 parts by weight); the content of a lubricant is usually 0.1 to 10 parts by weight (preferably, 0.5 to 3 parts by weight); and the content of a fluidizing agent is 0.1 to 10 parts by weight (preferably, 0.5 to 5 parts by weight).

As a liquid preparation for oral administration, for example, a solution, a syrup, an elixir, an emulsion or a suspending agent is mentioned. These liquid preparations may contain a crystal of the present invention together with pharmaceutically acceptable additives. As the additives, a suspending agent or an emulsifier is mentioned. These can be selected as necessary and mixed for producing drugs.

As a transmucosal agent for parenteral administration, such as an inhalant and a transnasal agent, a solid, liquid or semi-solid agent may be used and can be produced in accordance with a method known conventionally. For example, an excipient commonly known, and further, e.g., a pH modifier, a preservative, a surfactant, a lubricant, a stabilizer and a thickener may be appropriately added. For administration, an appropriate device for inhalation or insufflation can be used. A compound can be administered singly or as a powder of a prescribed mixture by using, for example, a device or a sprayer commonly known such as a metered-dosage inhalation device; or as a solution or suspension prepared in combination with a pharmaceutically acceptable carrier. The device such as a dry-powder inhaler may be one for single administration or a plurality of administrations, and can use a dry powder or a powder-containing capsule. The form of the inhaler may be a pressurized aerosol spray using an appropriate ejection agent such as a gas suitable in use, for example, chlorofluoroalkane, hydrofluoroalkane or carbon dioxide.

The pharmaceutical composition of the present invention can be administered to warm blooded animals (particularly humans). The dose of an active ingredient, i.e., crystal-form compound (I) or a pharmaceutically acceptable salt thereof, may vary depending on the various conditions of the patient, such as symptoms, age and body weight. For example, in the case of oral administration, the composition of the invention can be administered in a dose of 0.1 mg/body to 30 mg/body (preferably, 0.5 mg/body to 10 mg/body) per time, one to three times per day to a human in accordance with symptoms.

BRIEF DESCRIPTION OF DRAWINGS

FIG. 1 The figure shows the powder X-ray diffraction pattern of the crystal of Example 1. The ordinate axis of the figure represents diffraction intensity in terms of relative line intensity (counts); and the abscissa axis represents the value of a diffraction angle 2θ.

FIG. 2 The figure shows the powder X-ray diffraction pattern of the crystal of Example 2. The ordinate axis of the figure represents diffraction intensity in terms of relative line intensity (counts); and the abscissa axis represents diffraction angle 2θ.

FIG. 3 The figure shows the powder X-ray diffraction pattern of the crystal of Example 3. The ordinate axis of the figure represents diffraction intensity in terms of relative line intensity (counts); and the abscissa axis represents diffraction angle 2θ.

FIG. 4 The figure shows the powder X-ray diffraction pattern of the crystal of Example 4. The ordinate axis of the figure represents diffraction intensity in terms of relative line intensity (counts); and the abscissa axis represents diffraction angle 2θ.

FIG. 5 The figure shows the powder X-ray diffraction pattern of the crystal of Example 5. The ordinate axis of the figure represents diffraction intensity in terms of relative line intensity (counts); and the abscissa axis represents diffraction angle 2θ.

FIG. 6 The figure shows the powder X-ray diffraction pattern of the crystal of Example 6. The ordinate axis of the figure represents diffraction intensity in terms of relative line intensity (counts); and the abscissa axis represents diffraction angle 2θ.

FIG. 7 The figure shows the powder X-ray diffraction pattern of the crystal of Example 7. The ordinate axis of the figure represents diffraction intensity in terms of relative line intensity (counts); and the abscissa axis represents diffraction angle 2θ.

FIG. 8 The figure shows the powder X-ray diffraction pattern of the crystal of Example 8. The ordinate axis of the figure represents diffraction intensity in terms of relative line intensity (counts); and the abscissa axis represents diffraction angle 2θ.

FIG. 9 The figure shows the powder X-ray diffraction pattern of the crystal of Example 9. The ordinate axis of the figure represents diffraction intensity in terms of relative line intensity (counts); and the abscissa axis represents diffraction angle 2θ.

FIG. 10 The figure shows the powder X-ray diffraction pattern of the crystal of Example 10. The ordinate axis of the figure represents diffraction intensity in terms of relative line intensity (counts); and the abscissa axis represents diffraction angle 2θ.

FIG. 11 The figure shows the powder X-ray diffraction pattern of the crystal of Example 11. The ordinate axis of the figure represents diffraction intensity in terms of relative line intensity (counts); and the abscissa axis represents diffraction angle 2θ.

FIG. 12 The figure shows the powder X-ray diffraction pattern of the crystal of Example 12. The ordinate axis of the figure represents diffraction intensity in terms of relative line intensity (counts); and the abscissa axis represents diffraction angle 2θ.

FIG. 13 The figure shows the powder X-ray diffraction pattern of the crystal of Example 13. The ordinate axis of the figure represents diffraction intensity in terms of relative line intensity (counts); and the abscissa axis represents diffraction angle 2θ.

FIG. 14 The figure shows the gravimetric-differential thermal analysis (TG/DTA) chart of the crystal of Example 1. In the chart, the abscissa axis represents temperature (° C.); the right ordinate axis represents mass loss (wt %); and the left abscissa axis represents endothermic (exothermic) heat flow (μV).

FIG. 15 The figure shows the gravimetric-differential thermal analysis (TG/DTA) chart of the crystal of Example 2. In the chart, the abscissa axis represents temperature (° C.); the right ordinate axis represents mass loss (wt %); and the left abscissa axis represents endothermic (exothermic) heat flow (μV).

FIG. 16 The figure shows the gravimetric-differential thermal analysis (TG/DTA) chart of the crystal of Example 3. In the chart, the abscissa axis represents temperature (° C.); the right ordinate axis represents mass loss (wt %); and the left abscissa axis represents endothermic (exothermic) heat flow (μV).

FIG. 17 The figure shows the gravimetric-differential thermal analysis (TG/DTA) chart of the crystal of Example 4. In the chart, the abscissa axis represents temperature (° C.); the right ordinate axis represents mass loss (wt %); and the left abscissa axis represents endothermic (exothermic) heat flow (μV).

FIG. 18 The figure shows the gravimetric-differential thermal analysis (TG/DTA) chart of the crystal of Example 5. In the chart, the abscissa axis represents temperature (° C.); the right ordinate axis represents mass loss (wt %); and the left abscissa axis represents endothermic (exothermic) heat flow (μV).

FIG. 19 The figure shows the differential scanning calorimetry (DSC) chart of the crystal of Example 6. In the chart, the abscissa axis represents temperature (° C.); the left abscissa axis represents heat flowmass loss (W/g).

FIG. 20 The figure shows the gravimetric-differential thermal analysis (TG/DTA) chart of the crystal of Example 7. In the chart, the abscissa axis represents temperature (° C.); the left ordinate axis represents mass loss (wt %); and the right abscissa axis represents endothermic (exothermic) heat flow (μV).

FIG. 21 The figure shows the gravimetric-differential thermal analysis (TG/DTA) chart of the crystal of Example 8. In the chart, the abscissa axis represents temperature (° C.); the right ordinate axis represents mass loss (wt %); and the left abscissa axis represents endothermic (exothermic) heat flow (μV).

FIG. 22 The figure shows the gravimetric-differential thermal analysis (TG/DTA) chart of the crystal of Example 9. In the chart, the abscissa axis represents temperature (° C.); the right ordinate axis represents mass loss (wt %); and the left abscissa axis represents endothermic (exothermic) heat flow (μV).

FIG. 23 The figure shows the gravimetric-differential thermal analysis (TG/DTA) chart of the crystal of Example 10. In the chart, the abscissa axis represents temperature (° C.); the right ordinate axis represents mass loss (wt %); and the left abscissa axis represents endothermic (exothermic) heat flow (μV).

FIG. 24 The figure shows the gravimetric-differential thermal analysis (TG/DTA) chart of the crystal of Example 11. In the chart, the abscissa axis represents temperature (° C.); the right ordinate axis represents mass loss (wt %); and the left abscissa axis represents endothermic (exothermic) heat flow (μV).

FIG. 25 The figure shows the gravimetric-differential thermal analysis (TG/DTA) chart of the crystal of Example 12. In the chart, the abscissa axis represents temperature (° C.); the right ordinate axis represents mass loss (wt %); and the left abscissa axis represents endothermic (exothermic) heat flow (μV).

FIG. 26 The figure shows the gravimetric-differential thermal analysis (TG/DTA) chart of the crystal of Example 13. In the chart, the abscissa axis represents temperature (° C.); the right ordinate axis represents mass loss (wt %); and the left abscissa axis represents endothermic (exothermic) heat flow (μV).

EXAMPLES

The present invention will be more specifically described by way of the Examples; however, the scope of the present invention is not limited by these.

Note that, abbreviations used in the Examples represent the following.

μg: microgram, mg: milligram, g: gram, μL: micro liter, mL: milliliter, L: liter, mmol: millimole, MHz: megahertz, μm: micrometer, rpm: revolution per minute (rotation speed/minute)

THF: tetrahydrofuran, DCM: dichloromethane, DMSO: dimethylsulfoxide, DMF: N,N-dimethylformamide, DIPEA: diisopropylethylamine DTA: differential thermal analysis TG: thermogravimetry RH: relative humidity 1. Powder X-Ray Measurement Conditions Examples 1 to 5, 8 to 13

Apparatus: High-power X-ray diffractometer RINT-TTR III with a horizontal beam method, manufactured by Rigaku Corporation Source: CuKα ray Wavelength: 1.54056 Å

Measurable diffraction angle (2θ) range: 2 to 40°

Sampling width: 0.02°

Scan speed: 20°/minute

Tube voltage: 50 kV

Tube current: 300 mA

Diffusion slit: 0.5 mm

Scattering slit: 0.5 mm

Light-receiving slit: 0.5 mm

Examples 6,7

Apparatus: Desktop X-ray diffractometer MiniFlex300/600 manufactured by Rigaku Corporation
Source: CuKα ray
Wavelength: 1.541862 Å
Measurable diffraction angle (2θ) range: 3 to 50°
Sampling width: 0.02°
Scan speed: 10°/minute
Tube voltage: 40 kV
Tube current: 15 mA The measurements and analyses were performed according to the procedure described in the instruction. Note that, diffraction angle and diffraction intensity vary slightly depending on, e.g., the direction of crystal growth thereof, particle size and measurement conditions.

2. Conditions of Thermal Analysis (TG/DTA, DSC)

Examples 1 to 5, 7 to 13

Apparatus: TG/DTA6200, manufactured by SII Nanotechnology Inc.
Heating rate: 10° C./min
Atmosphere gas: nitrogen
Nitrogen-gas flow rate: 200 mL/min

Examples 6

Apparatus: DSC Q100 V9.9 Bulid303 manufactured by TA Instruments
An aluminum sample pan was filled with a sample (about 4 mg) and subjected to measurement under the nitrogen atmosphere (200 mL/minute) within the measurement range of 30° C. to 330° C. at a heating rate of 10° C./minute. Difference in temperature of a sample and a reference (vacant aluminum sample pan) was continuously measured and heat capacity was calculated. The measurements and analyses were performed according to the procedure described in the instructions.

3. Elemental Analysis Equipment

Apparatus: for CHN: organic elemental analysis microcoder JM10, J-SCIENCE LAB Co., Ltd.
Apparatus: for CHN: CHN CORDER Type MT-6, Yanako Technical Science
Apparatus: for F: ICS-1500-1 Ion Chromatography, DIONEX Corporation Nuclear magnetic resonance (hereinafter, referred to as $^1$H NMR) spectra were obtained by using tetramethylsilane as standard substance and a chemical shift value was described by a δ value (ppm). With respect to splitting patterns, a singlet was represented by s, doublet by d (double doublet by dd), multiplet by m, and broad singlet by brs.

Example 1

Production of Crystal of [2-(1-methyl-1H-pyrazol-4-yl)-6-(morpholin-4-yl)-9H-purin-8-yl][4-(morpholin-4-yl)piperidin-1-yl]methanone

[Formula 2]

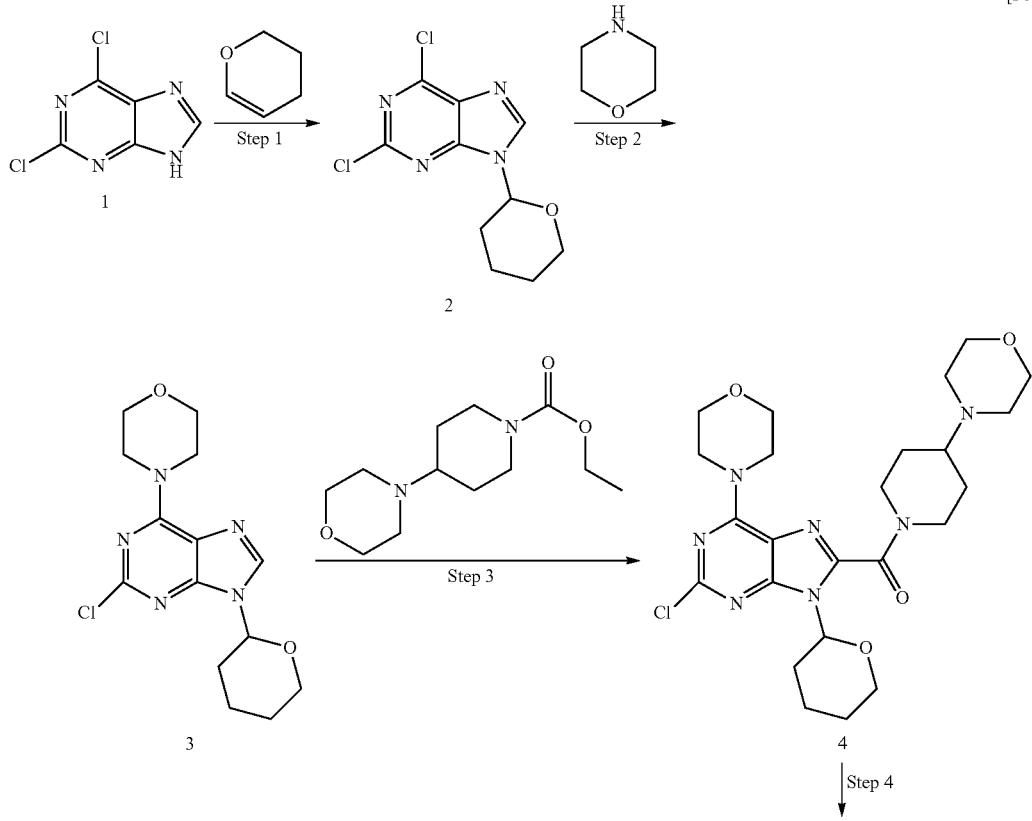

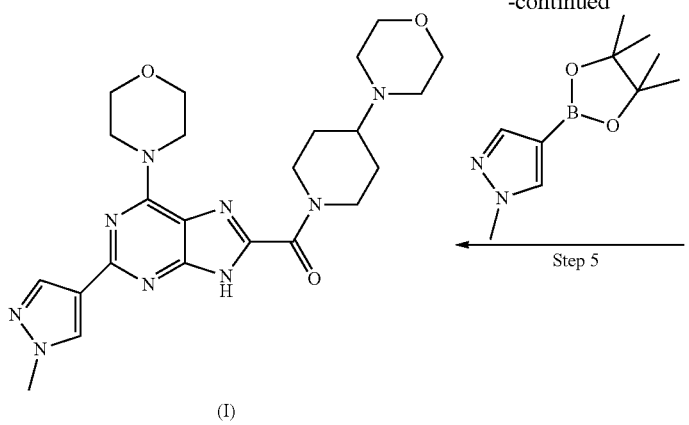

(I)

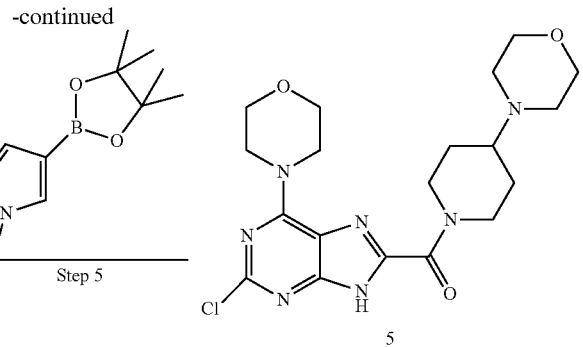

5

Step 1: Production of 2,6-dichloro-9-(tetrahydro-2H-pyran-2-yl)-9H-purine (2)

To a solution of 2,6-dichloro-9H-purine (50 g, 264.5 mmol) in ethyl acetate (500 ml), p-toluenesulfonic acid monohydrate (1.36 g, 7.92 mmol) was added and subsequently 3,4-dihydro-2H-pyran (55.36 g, 661.4 mmol) was added by use of a dropping funnel. Thereafter, the reaction solution was stirred at 70-80° C. for 4 hours, cooled to room temperature. To this, ammonia (15 ml) was added and the solution was stirred for 15 minutes. Subsequently, water (400 ml) was added to the solution, which was extracted with ethyl acetate (300 ml×3). The organic layer was dried over sodium sulfate and concentrated under reduced pressure. The resultant residue was put in hexane (500 ml) and stirred. The solid substance precipitated was filtered and dried under reduced pressure to obtain the title compound (70 g).

$^1$H NMR (400 MHz, DMSO-d$_6$) δ ppm: 8.96 (s, 1H), 5.75 (dd, J=2.01, 10.79 Hz, 1H), 3.99-4.12 (m, 1H), 3.69-3.83 (m, 1H), 2.20-2.34 (m, 1H), 1.93-2.07 (m, 2H), 1.69-1.84 (m, 1H), 1.39-1.67 (m, 2H).

Step 2: Production of 2-chloro-6-(morpholin-4-yl)-9-(tetrahydro-2H-pyran-2-yl)-9H-purine (3)

To a solution of 2,6-dichloro-9-(tetrahydro-2H-pyran-2-yl)-9H-purine (17 g, 62.2 mol) in methanol 300 ml), morpholine (11.92 g, 136.9 mol) was added at 0° C. The reaction solution was stirred at room temperature for 3 hours. After the solvent was evaporated under reduced pressure, water (300 ml) was added. The resultant solution was extracted with dichloromethane (500 ml×3). The organic layer was dried over sodium sulfate and then concentrated under reduced pressure to obtain the title compound (20 g).

$^1$H NMR (400 MHz, DMSO-d$_6$) δ ppm: 8.42 (s, 1H), 5.60 (dd, J=2.13, 10.92 Hz, 1H), 4.01 (dd, J=1.76, 10.79 Hz, 2H), 3.64-3.77 (m, 7H), 2.51 (td, J=1.76, 3.51 Hz, 1H), 2.11-2.25 (m, 1H), 1.90-2.01 (m, 2H), 1.69-1.81 (m, 1H), 1.53-1.62 (m, 2H).

Step 3: Production of [2-chloro-6-(morpholin-4-yl)-9-(tetrahydro-2H-pyran-2-yl)-9H-purin-8-yl][4-(morpholin-4-yl)piperidin-1-yl]methanone (4)

To a solution of 2,6-dichloro-9-(tetrahydro-2H-pyran-2-yl)-9H-purine (1 g, 3.09 mol) in tetrahydrofuran (70 ml) and ethyl-4-(morpholin-4-yl)piperidine-1-carboxylate (2.2 g, 9.28 mol), which was produced by the method described below, a tetrahydrofuran solution of (4.6 ml, 9.28 mol) of lithium diisopropylamide (2M) was added dropwise at −78° C. and the resultant reaction solution was stirred for 30 minutes, and then at room temperature for 90 minutes. The reaction solution was poured in a saturated ammonium chloride solution (100 ml), which was then extracted with ethyl acetate (150 ml×2). The organic layer was dried over sodium sulfate and concentrated under reduced pressure. The resultant residue was purified with flash chromatography (2-5% methanol/dichloromethane) to obtain the title compound (1.07 g).

$^1$H NMR (400 MHz, CDCl$_3$) δ ppm: 5.67-5.84 (m, 1H), 4.57-4.85 (m, 1H), 3.95-4.55 (m, 5H), 3.80 (t, J=3.76 Hz, 4H), 3.52-3.77 (m, 7H), 2.80-3.18 (m, 2H), 2.48-2.64 (m, 5H), 2.45 (td, J=3.45, 7.15 Hz, 1H), 1.98 (br. s., 4H), 1.96 (m, 4H).

Production of ethyl-4-(morpholin-4-yl)piperidine-1-carboxylate

To an acetonitrile/dichloromethane solution (100: ml), morpholine piperidine (5 g, 29.2 mol; manufactured by AK Scientific), triethylamine (5.9 g, 58.5 mmol) was added at room temperature. The reaction solution was cooled to 0° C. To this, ethyl chloroformate (3.8 g, 35.1 mmol) was added and the resultant solution was stirred at 0° C. for 10 minutes, and then at room temperature for 2-3 hours. After completion of the reaction, the reaction mixture was filtered. To the filtrate, water (400 ml) was added and the resultant solution was extracted with dichloromethane (500 ml×2). The organic layer was dried over sodium sulfate and concentrated under reduced pressure to obtain the title compound (5.8 g).

$^1$H NMR (400 MHz, DMSO-d$_6$) δ ppm: 3.86-4.09 (q, 2H), 3.86-4.09 (bs, 2H), 3.50-3.62 (m, 4H), 2.76 (br. s., 2H), 2.36-2.46 (m, 4H), 2.30 (tt, J=3.54, 11.01 Hz, 1H), 1.65-1.82 (m, 2H), 1.05-1.35 (m, 2H), 1.05-1.35 (t, 3H).

Step 4: Production of [2-chloro-6-(morpholin-4-yl)-9H-purine-8-yl][4-(morpholin-4-yl)piperidin-1-yl]methanone (5)

To a solution of [2-chloro-6-(morpholin-4-yl)-9-(tetrahydro-2H-pyran-2-yl)-9H-purin-8-yl][4-(morpholin-4-yl)piperidin-1-yl]methanone (400 mg, 0.77 mmol) in ethanol (15 ml), p-toluenesulfonic acid monohydrate (146 mg, 0.77 mmol) was added. The resultant solution was heated to reflux for 2 hours. When the reaction solution was checked by TLC, unreacted starting substance was detected. Then, p-toluenesulfonic acid monohydrate (43 mg, 0.23 mmol) was added to the reaction solution and heated to reflux for one hour. The reaction solution was cooled to room temperature and a saturated aqueous sodium bicarbonate solution (100 ml) was added to the solution. The solution was extracted with dichloromethane (150 ml×2). The organic layer was dried over sodium sulfate and concentrated under reduced pressure. The resultant residue was put in hexane and stirred. The solid substance precipitated was filtered and dried under reduced pressure to obtain the title compound (290 mg).

$^1$H NMR (400 MHz, DMSO-$d_6$) δ ppm: 13.57-14.14 (m, 1H), 4.88 (d, J=14.15 Hz, 1H), 4.46 (d, J=13.39 Hz, 1H), 4.01 (br s, 5H), 3.73 (t, J=4.55 Hz, 4H), 3.49-3.63 (m, 4H), 3.23 (t, J=11.62 Hz, 1H), 2.84-2.95 (m, 1H), 2.41-2.49 (m, 4H), 1.75-1.96 (m, 2H), 1.24-1.51 (m, 2H).

Step 5: Production of [2-(1-methyl-1H-pyrazol-4-yl)-6-(morpholin-4-yl)-9H-purin-8-yl][4-(morpholin-4-yl)piperidin-1-yl]methanone (5)

To a solution of [2-chloro-6-(morpholin-4-yl)-9H-purine-8-yl][4-(morpholin-4-yl)piperidin-1-yl]methanone (200 mg, 0.46 mmol) in acetonitrile (4 ml), 1-methyl 4-pyrazole boronic acid pinacol ester (143 g, 0.69 mmol), an aqueous sodium carbonate solution (121.55 mg, 1.1 mmol, 2 ml) and [1,1'-bis(diphenylphosphino)ferrocene]palladium (II) dichloride (18.7 mg, 0.022 mmol) were added and purged with argon gas for 15 minutes. Then, the reaction mixture was stirred at 140° C. for 8-10 hours, cooled to room temperature and thereafter water (80 ml) was added thereto. The mixture was extracted with 10% methanol/dichloromethane (100 ml×2). The organic layer was dried over sodium sulfate and concentrated under reduced pressure. The residue was purified by flash chromatography (8-20% methanol/dichloromethane) and concentrated under reduced pressure to obtain a crystal of the title compound (183 mg). The crystal was subjected to measurement by powder X-ray diffraction and NMR measurement.

$^1$H NMR (400 MHz, DMSO-$d_6$) δ ppm: 13.41-13.53 (m, $^1$H), 8.23 (s, 1H), 7.93 (s, 1H), 4.85-4.97 (m, 1H), 4.43-4.53 (m, 1H), 4.08-4.39 (m, 4H), 3.88 (s, 3H), 3.76 (d, J=4.77 Hz, 4H), 3.56 (d, J=4.27 Hz, 4H), 3.17-3.29 (m, 2H), 2.83-2.94 (m, 1H), 2.46 (d, J=5.02 Hz, 4H), 1.78-1.94 (m, 2H), 1.30-1.48 (m, 2H).

Table 1 describes diffraction angles (2θ), lattice spacing (D values) and relative intensities in the powder X-ray diffraction pattern.

TABLE 1

| Peak number | 2θ | D value | Relative intensity |
| --- | --- | --- | --- |
| 1 | 3.9 | 22.6 | 100 |
| 2 | 11.8 | 7.4 | 30 |
| 3 | 15.2 | 5.8 | 8 |
| 4 | 15.8 | 5.5 | 18 |
| 5 | 21.7 | 4.0 | 14 |
| 6 | 22.0 | 4.0 | 12 |
| 7 | 25.3 | 3.5 | 8 |

Example 2

Production of crystal of [2-(1-methyl-1H-pyrazol-4-yl)-6-(morpholin-4-yl)-9H-purin-8-yl][4-(morpholin-4-yl)piperidin-1-yl]methanone To the crystal (2.0 g) of [2-(1-methyl-1H-pyrazol-4-yl)-6-(morpholin-4-yl)-9H-purin-8-yl][4-(morpholin-4-yl)piperidin-1-yl]methanone produced in Example 1, 2,2,2-trifluoroethanol (200 ml) and DMSO (200 ml) were added at room temperature to completely dissolve the crystal. Using an evaporator, 2,2,2-trifluoroethanol was removed and the residue was frozen by an ultracold freezer (−80° C.) and lyophilized by a freeze dryer VirTis (Advantage Plus). To the resultant amorphous substance (2.0 g), water/methanol (3:97, 40 ml) was added. The mixture was stirred at room temperature for 3 days. The solid substance precipitated was obtained by filtration and dried at room temperature for 3 hours under reduced pressure to obtain a crystal (1.9 g (yield 95%)). The crystal was subjected to measurement by powder X-ray diffraction.

Table 2 describes diffraction angles (2θ), lattice spacing (D values) and relative intensities in the powder X-ray diffraction pattern.

TABLE 2

| Peak number | 2θ | D value | Relative intensity |
| --- | --- | --- | --- |
| 1 | 9.1 | 9.6 | 32 |
| 2 | 13.9 | 6.3 | 36 |
| 3 | 14.7 | 6.0 | 24 |
| 4 | 17.4 | 5.0 | 40 |
| 5 | 17.6 | 5.0 | 46 |
| 6 | 20.0 | 4.4 | 96 |
| 7 | 20.4 | 4.3 | 61 |
| 8 | 20.9 | 4.2 | 100 |

Example 3

Production of crystal of [2-(1-methyl-1H-pyrazol-4-yl)-6-(morpholin-4-yl)-9H-purin-8-yl][4-(morpholin-4-yl)piperidin-1-yl]methanone To the crystal (660 mg) of [2-(1-methyl-1H-pyrazol-4-yl)-6-(morpholin-4-yl)-9H-purin-8-yl][4-(morpholin-4-yl)piperidin-1-yl]methanone produced in Example 2, 1,4-dioxane (66 mL) was added to completely dissolve the crystal. This solution was dispensed to 21 glass test tubes at 2 mL per tube. The dispensed solution was frozen by ultracold freezer (−80° C.) and lyophilized by a freeze dryer, VirTis (Advantage Plus). To the resultant amorphous substance (20 mg), water (400 μL) was added. The mixture was stirred at 15° C. for 4 days and the solid substance precipitated was obtained by filtration. The same operation was repeated further two times. The solid substances obtained by filtration were combined and dried at room temperature for 3 hours under reduced pressure to obtain a crystal (60 mg (yield 100%)). The crystal was subjected to measurement by powder X-ray diffraction.

Table 3 describes diffraction angles (2θ), lattice spacing (D values) and relative intensities in the powder X-ray diffraction pattern.

TABLE 3

| Peak number | 2θ | D value | Relative intensity |
| --- | --- | --- | --- |
| 1 | 4.6 | 19.1 | 100 |
| 2 | 10.6 | 8.3 | 8 |
| 3 | 13.3 | 6.6 | 12 |
| 4 | 14.8 | 5.9 | 7 |
| 5 | 19.8 | 4.4 | 7 |
| 6 | 20.8 | 4.2 | 8 |
| 7 | 22.6 | 3.9 | 12 |

Example 4

Production of crystal of [2-(1-methyl-1H-pyrazol-4-yl)-6-(morpholin-4-yl)-9H-purin-8-yl][4-(morpholin-4-yl)piperidin-1-yl]methanone To the crystal (660 mg) of [2-(1-methyl-1H-pyrazol-4-yl)-6-(morpholin-4-yl)-9H-purin-8-yl][4-(morpholin-4-yl)piperidin-1-yl]methanone produced in Example 2, 1,4-dioxane (66 mL) was added to completely dissolve the crystal. The solution was dispensed to 21 glass test tubes at 2 mL per tube.

The content was frozen by an ultracold freezer (−80° C.) and lyophilized by a freeze dryer, VirTis (Advantage Plus). To the resultant amorphous substance (20 mg), 1-PrOH (400 µL) was added. The mixture was stirred at 15° C. for 3 days and the solid substance precipitated was obtained by filtration. Thereafter, the solid substance was dried at room temperature for 3 hours under reduced pressure to obtain a crystal (20 mg (yield 100%)). The crystal was subjected to measurement by powder X-ray diffraction.

Table 4 describes diffraction angles (2θ), lattice spacing (D values) and relative intensities in the powder X-ray diffraction pattern.

TABLE 4

| Peak number | 2θ | D value | Relative intensity |
| --- | --- | --- | --- |
| 1 | 6.9 | 12.7 | 22 |
| 2 | 15.2 | 5.8 | 23 |
| 3 | 17.4 | 5.0 | 27 |
| 4 | 18.0 | 4.9 | 31 |
| 5 | 18.8 | 4.6 | 28 |
| 6 | 20.8 | 4.2 | 17 |
| 7 | 21.5 | 4.1 | 100 |
| 8 | 27.2 | 3.2 | 18 |

Example 5

Production of crystal of [2-(1-methyl-1H-pyrazol-4-yl)-6-(morpholin-4-yl)-9H-purin-8-yl][4-(morpholin-4-yl)piperidin-1-yl]methanone The crystal (11 mg) of [2-(1-methyl-1H-pyrazol-4-yl)-6-(morpholin-4-yl)-9H-purin-8-yl][4-(morpholin-4-yl)piperidin-1-yl]methanone produced in Example 1 was placed in an aluminum pan for thermogravimetric differential thermal analyzer (TG-DTA) and heated by the thermogravimetric analyzer at a heating rate of 10° C. per minute from room temperature to 230° C., and then, the aluminum pan was immediately taken out. The resulted crystal obtained from the aluminum pan. After this operation was repeated about 100 times, the crystal (1.1 g) was obtained. The crystal was subjected to measurement by powder X-ray diffraction.

Table 5 describes diffraction angles (2θ), lattice spacing (D values) and relative intensities in the powder X-ray diffraction pattern.

TABLE 5

| Peak number | 2θ | D value | Relative intensity |
| --- | --- | --- | --- |
| 1 | 7.2 | 12.1 | 31 |
| 2 | 8.7 | 10.1 | 16 |
| 3 | 17.6 | 5.0 | 30 |
| 4 | 18.5 | 4.7 | 71 |
| 5 | 20.0 | 4.4 | 21 |
| 6 | 20.9 | 4.2 | 28 |
| 7 | 21.7 | 4.0 | 29 |

Example 6

Production of crystal of [2-(1-methyl-1H-pyrazol-4-yl)-6-(morpholin-4-yl)-9H-purin-8-yl][4-(morpholin-4-yl)piperidin-1-yl]methanone The [2-(1-methyl-1H-pyrazol-4-yl)-6-(morpholin-4-yl)-9H-purin-8-yl][4-(morpholin-4-yl)piperidin-1-yl]methanone (5 g) produced in Example 1 was purified by column chromatography (5-10% methanol (containing 3% ammonia)/dichloromethane). The solution was concentrated under reduced pressure and the residue was suspended in dichloromethane (300 ml), methanol (25 ml) and MPTMT resin (2.5 g) and stirred for 5-6 hours. After completion of stirring, the solution obtained by filtering out the resin was concentrated under reduced pressure. To the concentrate, hexane (300 ml) was added. The resultant solution was filtered and dried at 50° C. to obtain a crystal (5 g). The crystal was subjected to measurement by powder X-ray diffraction.

Table 6 describes diffraction angles (2θ), lattice spacing (D values) and relative intensities in the powder X-ray diffraction pattern.

TABLE 6

| Peak number | 2θ | D value | Relative intensity |
| --- | --- | --- | --- |
| 1 | 4.1 | 21.5 | 57 |
| 2 | 8.3 | 10.6 | 41 |
| 3 | 10.0 | 8.8 | 29 |
| 4 | 12.4 | 7.1 | 100 |
| 5 | 15.5 | 5.7 | 48 |
| 6 | 16.4 | 5.4 | 89 |
| 7 | 17.9 | 4.9 | 14 |
| 8 | 18.4 | 4.8 | 33 |

Example 7

Production of crystal of [2-(1-methyl-1H-pyrazol-4-yl)-6-(morpholin-4-yl)-9H-purin-8-yl][4-(morpholin-4-yl)piperidin-1-yl]methanone To [2-(1-methyl-1H-pyrazol-4-yl)-6-(morpholin-4-yl)-9H-purin-8-yl][4-(morpholin-4-yl)piperidin-1-yl]methanone (11.9 g) dissolved in dichloromethane (600 ml), methanol (100 ml) and MP-TMT resin (6.7 g) serving as a metal scavenger were added. The solution was stirred at room temperature for about 7 hours, filtered by use of Celite, and concentrated by an evaporator under reduced pressure. Thereafter, hexane (100 ml) was added to the solution, which was again concentrated under reduced pressure. After this operation was repeated 5 times, hexane (450 ml) was added. The solution was stirred for about 15 minutes. The solid substance precipitated was filtered and dried at 50° C. under reduced pressure to obtain a crystal. The crystal was subjected to measurement by powder X-ray diffraction.

Table 7 describes diffraction angles (2θ), lattice spacing (D values) and relative intensities in the powder X-ray diffraction pattern.

TABLE 7

| Peak number | 2θ | D value | Relative intensity |
| --- | --- | --- | --- |
| 1 | 3.9 | 22.1 | 99 |
| 2 | 12.0 | 7.3 | 54 |
| 3 | 15.2 | 5.8 | 100 |
| 4 | 16.3 | 5.4 | 44 |
| 5 | 21.2 | 4.1 | 35 |
| 6 | 21.6 | 4.1 | 92 |
| 7 | 22.1 | 4.0 | 66 |
| 8 | 24.4 | 3.6 | 56 |

Example 8

Production of crystal of p-toluenesulfonic acid salt of [2-(1-methyl-1H-pyrazol-4-yl)-6-(morpholin-4-yl)-9H-purin-8-yl][4-(morpholin-4-yl)piperidin-1-yl]methanone To the crystal (1.2 g) of [2-(1-methyl-1H-pyrazol-4-yl)-6-(morpholin-4-yl)-9H-purin-8-yl][4-(morpholin-4-yl)piperidin-1-yl]methanone produced in Example 1, water/acetonitrile (3: 97, 12 ml) was added and p-toluenesulfonic acid monohydrate (485 mg) was added. The solution was stirred at room temperature for 3 days. The solid substance precipitated was obtained by filtration and then dried for 3 hours under reduced pressure to obtain the title crystal (1.7 g). The crystal was subjected to measurement by powder X-ray diffraction and NMR measurements.

$^1$H NMR (500 MHz, DMSO-$d_6$): δ ppm: 13.57 (1H, brs), 8.24 (1H, s), 7.94 (1H, s), 7.49-7.46 (2H, m), 7.12-7.08 (2H, m), 5.29 (1H, d, J=12.47 Hz), 4.65 (1H, d, J=11.62 Hz), 4.25 (4H, brs), 4.03 (2H, d, J=11.90 Hz), 3.89 (3H, s), 3.76 (4H, dd, J=4.82 Hz), 3.70-3.64 (2H, m), 3.56 (1H, brs), 3.47 (2H, d, J=11.34 Hz), 3.23-3.11 (3H, m), 2.88-2.82 (1H, m), 2.51-2.49 (1H, m), 2.28 (3H, s), 2.22-2.14 (2H, m), 1.68-1.57 (2H, m)

Table 8 describes diffraction angles (2θ), lattice spacing (D values) and relative intensities in the powder X-ray diffraction pattern.

TABLE 8

| Peak number | 2θ | D value | Relative intensity |
| --- | --- | --- | --- |
| 1 | 2.8 | 31.3 | 100 |
| 2 | 5.6 | 15.7 | 11 |
| 3 | 8.4 | 10.4 | 18 |
| 4 | 11.2 | 7.8 | 43 |
| 5 | 15.0 | 5.8 | 24 |
| 6 | 21.4 | 4.1 | 24 |
| 7 | 22.9 | 3.8 | 25 |
| 8 | 25.7 | 3.4 | 18 |

Example 9

Production of Crystal of a Citric Acid Salt of [2-(1-methyl-1H-pyrazol-4-yl)-6-(morpholin-4-yl)-9H-purin-8-yl][4-(morpholin-4-yl)piperidin-1-yl]methanone To the crystal (50 mg) of [2-(1-methyl-1H-pyrazol-4-yl)-6-(morpholin-4-yl)-9H-purin-8-yl][4-(morpholin-4-yl)piperidin-1-yl]methanone produced in Example 2, ethanol (1000 μL) was added and a 1.000 mol/L aqueous citric acid solution (103.8 μL) was added. The solution was stirred at 40° C. for 3 days. The solid substance precipitated was filtered to obtain the title crystal (48 mg). The crystal was subjected to measurement by powder X-ray diffraction and NMR measurements.

$^1$H NMR (500 MHz, DMSO-$d_6$): δ ppm: 13.49 (1H, brs), 12.50-10.00 (2H, brs), 8.23 (1H, s), 7.93 (1H, s), 4.99 (1H, d, J=12.47 Hz), 4.51 (1H, d, J=13.32 Hz), 4.25 (4H, brs), 3.88 (3H, s), 3.76 (4H, dd, J=4.82 Hz), 3.62 (4H, dd, J=4.25 Hz), 3.25-3.20 (1H, m), 2.90-2.85 (1H, m), 2.73-2.59 (9H, m), 2.51-2.49 (2H, m), 1.98-1.90 (2H, m), 1.50-1.40 (2H, m)

Table 9 describes diffraction angles (2θ), lattice spacing (D values) and relative intensities in the powder X-ray diffraction pattern.

TABLE 9

| Peak number | 2θ | D value | Relative intensity |
| --- | --- | --- | --- |
| 1 | 6.5 | 13.4 | 100 |
| 2 | 9.5 | 9.2 | 23 |
| 3 | 10.6 | 8.3 | 69 |
| 4 | 14.5 | 6.0 | 65 |
| 5 | 15.1 | 5.8 | 44 |
| 6 | 17.0 | 5.1 | 49 |
| 7 | 20.7 | 4.2 | 27 |
| 8 | 26.3 | 3.3 | 25 |

Example 10

Production of Crystal of a Citric Acid Salt of [2-(1-methyl-1H-pyrazol-4-yl)-6-(morpholin-4-yl)-9H-purin-8-yl][4-(morpholin-4-yl)piperidin-1-yl]methanone To the crystal (1.2 g) of [2-(1-methyl-1H-pyrazol-4-yl)-6-(morpholin-4-yl)-9H-purin-8-yl][4-(morpholin-4-yl)piperidin-1-yl]methanone produced in Example 2, methanol (1000 μL) was added and 1.000 mol/L aqueous citric acid solution (103.8 μL) was added. The solution was stirred at 40° C. for 3 days. The solid substance precipitated was filtered to obtain the title crystal (53 mg). The crystal was subjected to measurement by powder X-ray diffraction and NMR measurements.

$^1$H NMR (500 MHz, DMSO-$d_6$): δ ppm: 13.48 (1H, brs), 12.50-10.00 (2H, brs), 8.23 (1H, s), 7.93 (1H, s), 4.99 (1H, d, J=12.75 Hz), 4.51 (1H, d, J=12.19 Hz), 4.25 (4H, brs), 3.88 (3H, s), 3.76 (4H, dd, J=4.82 Hz), 3.62 (4H, dd, J=4.39 Hz), 3.25-3.20 (1H, m), 2.90-2.85 (1H, m), 2.73-2.59 (9H, m), 2.51-2.49 (2H, m), 1.98-1.90 (2H, m), 1.51-1.38 (2H, m)

Table 10 describes diffraction angles (2θ), lattice spacing (D values) and relative intensities in the powder X-ray diffraction pattern.

TABLE 10

| Peak number | 2θ | D value | Relative intensity |
| --- | --- | --- | --- |
| 1 | 4.5 | 19.2 | 21 |
| 2 | 6.4 | 13.6 | 100 |
| 3 | 9.1 | 9.6 | 37 |
| 4 | 10.2 | 8.5 | 55 |
| 5 | 13.5 | 6.5 | 51 |
| 6 | 14.5 | 6.0 | 45 |
| 7 | 16.9 | 5.2 | 42 |
| 8 | 25.8 | 3.4 | 32 |

Example 11

Production of Crystal of an Oxalic Acid Salt of [2-(1-methyl-1H-pyrazol-4-yl)-6-(morpholin-4-yl)-9H-purin-8-yl][4-(morpholin-4-yl)piperidin-1-yl]methanone To the crystal (330 mg) of [2-(1-methyl-1H-pyrazol-4-yl)-6-(morpholin-4-yl)-9H-purin-8-yl][4-(morpholin-4-yl)piperidin-1-yl]methanone produced in Example 2, dioxane (66 mL) was added to dissolve the crystal. This solution (20 mL) was dispensed to an eggplant shaped flask and a 0.500 mol/L aqueous oxalic acid solution (416 μL) was added to the flask. The content was frozen by an ultracold freezer (−80° C.) and lyophilized by a freeze dryer VirTis (Advantage Plus). To the resultant amorphous substance, water/methanol (3: 97, 2 ml) was added. The mixture was stirred at room temperature for 12 days. The solid substance precipitated was obtained by filtration. The obtained crystal was dried in the air for one day to obtain the title crystal (97 mg). The crystal was subjected to measurement by powder X-ray diffraction and NMR measurements.

$^1$H NMR (500 MHz, DMSO-$d_6$): δ ppm: 13.49 (1H, brs), 8.24 (1H, s), 7.93 (1H, s), 5.09 (1H, d, J=12.52 Hz), 4.55 (1H, d, J=13.17 Hz), 4.29-4.24 (4H, brs), 3.89 (3H, s), 3.76 (4H, dd, J=4.82 Hz), 3.70 (4H, dd, J=3.85 Hz), 3.24-3.19 (1H, m), 2.98 (1H, brs), 2.95-2.85 (5H, m), 2.51-2.49 (2H, m), 2.06-1.99 (2H, m), 1.59-1.45 (2H, m)

Table 11 describes diffraction angles (2θ), lattice spacing (D values) and relative intensities in the powder X-ray diffraction pattern.

TABLE 11

| Peak number | 2θ | D value | Relative intensity |
| --- | --- | --- | --- |
| 1 | 3.2 | 27.4 | 54 |
| 2 | 11.6 | 7.6 | 28 |
| 3 | 15.2 | 5.8 | 91 |
| 4 | 16.6 | 5.3 | 37 |
| 5 | 16.9 | 5.2 | 34 |
| 6 | 22.5 | 3.9 | 100 |
| 7 | 25.3 | 3.5 | 30 |
| 8 | 26.1 | 3.4 | 32 |

Example 12

Production of crystal of a glutaric acid salt of [2-(1-methyl-1H-pyrazol-4-yl)-6-(morpholin-4-yl)-9H-purin-8-yl][4-(morpholin-4-yl)piperidin-1-yl]methanone To the crystal (330 mg) of [2-(1-methyl-1H-pyrazol-4-yl)-6-(morpholin-4-yl)-9H-purin-8-yl][4-(morpholin-4-yl)piperidin-1-yl]methanone produced in Example 2, dioxane (66 mL) was added to dissolve the crystal. This solution (20 mL) was dispensed to an eggplant shaped flask and a 1.000 mol/L aqueous glutaric acid solution (208 μL) was added to the flask. The content was frozen by an ultracold freezer (−80° C.) and lyophilized by a freeze dryer VirTis (Advantage Plus). To the resultant amorphous substance, ethanol (2 mL) was added. The mixture was stirred at room temperature for 3 days. The solid substance precipitated was obtained by filtration. The obtained crystal was dried in the air for one day to obtain the title crystal (101 mg). The crystal was subjected to measurement by powder X-ray diffraction and NMR measurements.

$^1$H NM (500 MHz, DMSO-$d_6$): δ ppm: 13.46 (1H, brs), 12.05 (2H, brs), 8.23 (1H, s), 7.93 (1H, s), 4.92 (1H, d, J=12.75 Hz), 4.47 (1H, d, J=12.47 Hz), 4.25 (4H, brs), 3.89 (3H, s), 3.75 (4H, dd, J=4.82 Hz), 3.57 (4H, dd, J=4.54 Hz), 3.26-3.20 (1H, m), 2.91-2.85 (1H, m), 2.51-2.47 (5H, m), 2.26-2.22 (4H, m), 1.92-1.83 (2H, m), 1.73-1.67 (2H, m), 1.48-1.33 (2H, m)

Table 12 describes diffraction angles (2θ), lattice spacing (D values) and relative intensities in the powder X-ray diffraction pattern.

TABLE 12

| Peak number | 2θ | D value | Relative intensity |
| --- | --- | --- | --- |
| 1 | 5.6 | 15.6 | 37 |
| 2 | 8.7 | 10.1 | 51 |
| 3 | 11.2 | 7.8 | 60 |
| 4 | 17.5 | 5.0 | 43 |
| 5 | 18.4 | 4.8 | 54 |
| 6 | 21.5 | 4.1 | 63 |
| 7 | 22.7 | 3.9 | 47 |
| 8 | 24.9 | 3.5 | 100 |

Example 13

Production of crystal of a malic acid salt of [2-(1-methyl-1H-pyrazol-4-yl)-6-(morpholin-4-yl)-9H-purin-8-yl][4-(morpholin-4-yl)piperidin-1-yl]methanone To the crystal (1.2 g) of [2-(1-methyl-1H-pyrazol-4-yl)-6-(morpholin-4-yl)-9H-purin-8-yl][4-(morpholin-4-yl)piperidin-1-yl]methanone produced in Example 2, dioxane (66 mL) was added to dissolve the crystal. This solution (20 mL) was dispensed to an eggplant shaped flask and a 1.000 mol/L aqueous malic acid solution (208 μL) was added to the flask. The content was frozen by an ultracold freezer (−80° C.) and lyophilized by a freeze dryer VirTis (Advantage Plus). To the resultant amorphous substance, methanol (2 mL) was added. The mixture was stirred at room temperature for 3 days. The solid substance precipitated was obtained by filtration. The obtained crystal was dried in the air for one day to obtain the title crystal (102 mg). The crystal was subjected to measurement by powder X-ray diffraction and NMR measurements.

$^1$H NMR (500 MHz, DMSO-$d_6$): δ ppm: 13.47 (1H, brs), 12.50-9.00 (1H, brs), 8.23 (1H, s), 7.93 (1H, s), 4.95 (1H, d, J=13.04 Hz), 4.49 (1H, d, J=12.75 Hz), 4.24 (4H, brs), 4.22-4.19 (1H, m), 3.88 (3H, s), 3.75 (4H, dd, J=4.82 Hz), 3.59 (4H, dd, J=4.54 Hz), 3.26-3.20 (1H, m), 2.90-2.85 (1H, m), 2.62-2.39 (9H, m), 1.95-1.86 (2H, m), 1.50-1.35 (2H, m)

Table 13 describes diffraction angles (2θ), lattice spacing (D values) and relative intensities in the powder X-ray diffraction pattern.

TABLE 13

| Peak number | 2θ | D value | Relative intensity |
| --- | --- | --- | --- |
| 1 | 4.6 | 18.9 | 26 |
| 2 | 9.3 | 9.4 | 100 |
| 3 | 9.6 | 9.1 | 76 |
| 4 | 14.1 | 6.2 | 14 |
| 5 | 15.4 | 5.7 | 100 |
| 6 | 20.6 | 4.2 | 20 |
| 7 | 25.0 | 3.5 | 33 |
| 8 | 27.8 | 3.2 | 25 |

[TG/DTA Measurement]

The crystals of Examples 1 to 13 were subjected to TG/DTA measurement. The results are shown in FIG. 14 to FIG. 26.

All crystals had a melting point of 200° C. or more and it was found that the crystals of Examples 1 to 13 had high thermal stability.

Test Example 1

In-Vitro Enzyme Assay

A Kinase-Glo luminescent kinase assay kit (manufactured by Promega) was used for measuring kinase activity. In this assay, the amount of ATP remaining in a solution after a kinase reaction was measured. To confirm the effect of a compound on PI3Kδ inhibition, 2.29 μg/ml recombinant PI3Kδ enzyme (Proteros, Germany) was added to a reaction mixture containing 10 mM $MgCl_2$, 5 mM DTT, 60 μM phosphatidylinositol diphosphate (PIP2) and an assay buffer (containing 50 mM HEPES, pH7.4, 50 mM NaCl, 0.05% CHAPS) supplemented with 10 μM ATP in a final volume of 15 μl/well, in the presence and absence of compound (I), in a 384-well plate. The reaction mixture was incubated at room temperature for 2 hours. At the end of the incubation period, the same volume of Kinase-Glo plus (Promega, V3772) was added per well. After the reaction mixture was incubated at room temperature for 10 minutes in a dark place, emission was measured. The results were calculated by measuring the emission unit of the test sample relative to a blank containing no enzyme.

Using specific recombinant enzymes (Proteros, Germany) PI3Kα, PI3Kβ and PI3Kγ, inhibitory activities of compound (I) against each of the kinases were examined. The assay conditions of kinases (PI3Kα, PI3Kβ, PI3Kγ and PI3Kδ) were as follows.

Enzyme: 2.29 μg/mL,
ATP: 10 μM,
PIP2 substrate: 60 μM
Reaction time: 2 hours
Brevity Codes:
HEPES: 2-[4-(2-hydroxyethyl)piperazin-1-yl]ethanesulfonic acid
CHAPS: 3-[(3-cholamidopropyl)dimethylammonio]-1-propanesulfonate
$MgCl_2$: magnesium chloride
PIP2: phosphatidylinositol 4,5-diphosphate
DTT: dithiothreitol
ATP: adenosine triphosphate The inhibitory activity ($IC_{50}$) of the compound (I) produced in accordance with Example 1 against PI3Kδ was 14 nM. The compound (I) had an extremely satisfactory inhibitory activity. In contrast, the inhibitory activity ($IC_{50}$) against other kinases were as follows: PI3Kα: 1000 nM or more, PI3Kβ: 10000 nM or more, PI3Kγ: 1000 nM or more. It was found that the compound (I) selectively inhibited PI3Kδ.

Test Example 2

Phytohaemagglutinin (PHA) Inducible Interferon (IFN)-Gamma Release in Mouse Splenocytes In a cell based assay system, the effect of a compound on mitogen-induced IFN-γ release in mouse splenocytes was evaluated [Blood (2010) 115: 2203 to 2213 pages; Current Protocols in Immunology (2004) 3.12.1 to 3.12.20].

Mouse splenocytes were obtained from the spleen of a C57BL/6 mouse and seeded in a 96-well tissue culture plate at a density of 250,000 cells/well. The splenocytes were treated with the compound (I), and thereafter, stimulated with PHA (10 μg/ml) for 48 hours. In this manner, an effect of compound (I) on inhibition of IFN-γ release was evaluated. The IFN-γ release in the cell culture supernatant was quantified by ELISA in accordance with the manufacturer's protocol (BD Biosciences, #555138).

The activity ($IC_{50}$) of the compound (I) was 6 nM. An extremely satisfactory result is shown.

Test Example 3

Method for Examining Therapeutic Effect

Test Example 3a

Ovalbumin-Induced Airway Eosinophilia Model in Brown Norway Rat

The protocol used herein was described in Clin. Exp. Immunol., 2001; 126: 9 to 15 pages and J. Pharmacol. Exp. Ther., 2011; 337: 145 to 54 pages.

A male Brown Norway rat was sensitized by intraperitoneally injecting a suspension (in 0.9% physiological saline sterilized) of ovalbumin (1 mg) and aluminum hydroxide (100 mg) on Day 0 and Day 7. On Day 14, the compound (I) was administered to the rat by oral gavage. One hour after the oral administration, the animal was housed in a Perspex chamber and exposed to 5% ovalbumin aerosol for 10 minutes. The compound (I) was administered once or twice a day on Day 14 and Day 15. Forty eight hours after ovalbumin challenge, the animal was euthanized and bronchoalveolar lavage fluid was collected. The cell suspension was treated, and the absolute number of eosinophils were counted.

The $ED_{50}$ value of the compound (I) was 0.3 mg/kg, bid. From this, it was confirmed that the compound (I) is effective.

Test Example 3b

House Dust Mite (HDM)-Induced Chronic Asthma Model of Balb/c Mouse

The protocol used herein was described in Am. J. Respir. Crit. Care Med., 2004; 169: 378 to 385 pages.

A female Balb/c mouse was intranasally exposed to a purified HDM (*Dermatophagoides pteronyssinus*) extract at maximum for 5 successive weeks at a frequency of 5 days/week (protein (25 μg) in physiological saline (20 μl)). The compound (I) was orally administered twice a day from the third week to fifth week. Forty eight hours after the final HDM exposure, the animal was euthanized and bronchoalveolar lavage fluid was collected. The cell suspension was treated, and the absolute number of eosinophils were counted.

The $ED_{50}$ value of the compound (I) was 0.1 mg/kg, bid. From this, it was confirmed that the compound (I) is effective.

Test Example 4

Method for Examining Oral Bioavailability (BA) in Rats and Mice

Test Example 4a

Oral Bioavailability (BA) in Rats

To a female Wistar rat (210±10 g), the compound (I) was intravenously administered as a solution containing the compound (I) (2.0 mg/mL) in a vehicle containing polysorbate and dextrose (pH5.0) or orally as a suspension of the compound (I) (1.0 mg/mL) in methyl cellulose. The final dosage in the case of intravenous administration was 3.0 mg/body weight (1 kg) or that in the case of oral administration was 10.0 mg/body weight (1 kg). A plasma sample was analyzed for the compound (I) by the LC-MS/MS method. Pharmacokinetic parameters were estimated by moment analysis. WinNonlin software 6.1 (Pharsight) was used for estimating the PK parameters. Oral bioavailability was calculated based on dose-normalized oral exposure and intravenous plasma exposure amounts.

Compound (I) showed sufficient bioavailability to be applied to an oral therapy. The bioavailability thereof was 88.

Test Example 4b

Oral Bioavailability (BA) in Mice

To a male Swiss mouse (23±3 g), the compound (I) was intravenously administered as a solution containing the compound (I) (0.3 mg/mL) in a vehicle containing polysorbate and dextrose (pH5.0) or orally as a suspension of the compound (I) (1.0 mg/mL) in methyl cellulose. The final dosage in the case of intravenous administration was 3.0 mg/body weight (1 kg) or that in the case of oral administration was 10.0 mg/body weight (1 kg). A plasma sample was analyzed for the compound (I) by the LC-MS/MS method. Pharmacokinetic parameters were estimated by moment analysis. WinNonlin software 6.1 (Pharsight) was used for estimating the PK parameters. Oral bioavailability was calculated based on dose-normalized oral exposure and intravenous plasma exposure amounts.

Compound (I) showed sufficient bioavailability to be applied to an oral therapy. The bioavailability thereof was 100.

Test Example 5

Method for Examining Solubility

A 10 mmol/L solution of the compound (I) in DMSO was prepared. The 10 mmol/L DMSO stock solution (100 μL) was dispensed to two labelled glass tubes: one for Solution 1 (JP1) according to the Japanese Pharmacopoeia and the other for Solution 2 (JP2) according to the Japanese Pharmacopoeia. DMSO was allowed to evaporate from each of the glass tubes, JP1 and JP2 solutions (500 μL) were added in the corresponding glass tubes. These glass tubes were ultrasonically treated for one minute and placed on a shaker for 30 minutes every 5 minutes at the intervals of 30 seconds. The glass tubes were placed in a dark place at room temperature for one hour and the solutions were filtered through a membrane filter. The filtrates were diluted 2 and 10 fold. The resultant test solutions were analyzed and quantified with UPLC (standard product: a 10 mmol/L solution in DMSO was serially diluted with a 50% aqueous acetonitrile solution to prepare two solutions: a 100 μmol/L standard solution and a 5 μmol/L standard solution) relative to the standard.

The solubility of compound (I) to JP1 was 1200 μg/mL or more and the solubility thereof to JP2 was 170 μg/mL. The compound (I) showed extremely satisfactory solubility.

The invention claimed is:
1. A crystal of [2-(1-methyl-1H-pyrazol-4-yl)-6-(morpholin-4-yl)-9H-purin-8-yl][4-(morpholin-4-yl)piperidin-1-yl] methanone having at least 5 peaks at diffraction angles (2θ) selected from 9.1±0.2, 13.9±0.2, 14.7±0.2, 17.4±0.2, 17.6±0.2, 20.0±0.2, 20.4±0.2 and 20.9±0.2 in powder X-ray diffraction using CuKα radiation.

2. A pharmaceutical composition comprising the crystal according to claim 1 and a pharmaceutically acceptable additive.

3. A treatment method for a disease treatable by inhibiting PI3Kδ, comprising administering the crystal according to claim 1 to a subject in need of treatment for a disease treatable by inhibiting PI3Kδ.

4. The treatment method according to claim 3, wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

5. A crystal of [2-(1-methyl-1H-pyrazol-4-yl)-6-(morpholin-4-yl)-9H-purin-8-yl][4-(morpholin-4-yl)piperidin-1-yl] methanone having at least 5 peaks at diffraction angles (2θ) selected from 4.6±0.2, 10.6±0.2, 13.3±0.2, 14.8±0.2, 19.8±0.2, 20.8±0.2 and 22.6±0.2 in powder X-ray diffraction using CuKα radiation.

6. A pharmaceutical composition comprising the crystal according to claim 5 and a pharmaceutically acceptable additive.

7. A treatment method for a disease treatable by inhibiting PI3Kδ, comprising administering the crystal according to claim 5 to a subject in need of treatment for a disease treatable by inhibiting PI3Kδ.

8. The treatment method according to claim 7, wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

9. A crystal of [2-(1-methyl-1H-pyrazol-4-yl)-6-(morpholin-4-yl)-9H-purin-8-yl][4-(morpholin-4-yl)piperidin-1-yl] methanone having at least 5 peaks at diffraction angles (2θ) selected from 6.9±0.2, 15.2±0.2, 17.4±0.2, 18.0±0.2, 18.8±0.2, 20.8±0.2, 21.5±0.2 and 27.2±0.2 in powder X-ray diffraction using CuKα radiation.

10. A pharmaceutical composition comprising the crystal according to claim 9 and a pharmaceutically acceptable additive.

11. A treatment method for a disease treatable by inhibiting PI3Kδ, comprising administering the crystal according to claim 9 to a subject in need of treatment for a disease treatable by inhibiting PI3Kδ.

12. The treatment method according to claim 11, wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

13. A crystal of [2-(1-methyl-1H-pyrazol-4-yl)-6-(morpholin-4-yl)-9H-purin-8-yl][4-(morpholin-4-yl)piperidin-1-yl]methanone having at least 5 peaks at diffraction angles (2θ) selected from 7.2±0.2, 8.7±0.2, 17.6±0.2, 18.5±0.2, 20.0±0.2, 20.9±0.2 and 21.7±0.2 in powder X-ray diffraction using CuKα radiation.

14. A pharmaceutical composition comprising the crystal according to claim 13 and a pharmaceutically acceptable additive.

15. A treatment method for a disease treatable by inhibiting PI3Kδ, comprising administering the crystal according to claim 13 to a subject in need of treatment for a disease treatable by inhibiting PI3Kδ.

16. The treatment method according to claim 15, wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

17. A crystal of [2-(1-methyl-1H-pyrazol-4-yl)-6-(morpholin-4-yl)-9H-purin-8-yl][4-(morpholin-4-yl)piperidin-1-yl]methanone having at least 5 peaks at diffraction angles (2θ) selected from 4.1±0.2, 8.3±0.2, 10.0±0.2, 12.4±0.2, 15.5±0.2, 16.4±0.2, 17.9±0.2 and 18.4±0.2 in powder X-ray diffraction using CuKα radiation.

18. A pharmaceutical composition comprising the crystal according to claim 17 and a pharmaceutically acceptable additive.

19. A treatment method for a disease treatable by inhibiting PI3Kδ, comprising administering the crystal according to claim 17 to a subject in need of treatment for a disease treatable by inhibiting PI3Kδ.

20. The treatment method according to claim 19, wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

21. A crystal of [2-(1-methyl-1H-pyrazol-4-yl)-6-(morpholin-4-yl)-9H-purin-8-yl][4-(morpholin-4-yl)piperidin-1-yl]methanone having at least 5 peaks at diffraction angles (2θ) selected from 3.9±0.2, 12.0±0.2, 15.2±0.2, 16.3±0.2, 21.2±0.2, 21.6±0.2, 22.1±0.2 and 24.4±0.2 in powder X-ray diffraction using CuKα radiation.

22. A pharmaceutical composition comprising the crystal according to claim 21 and a pharmaceutically acceptable additive.

23. A treatment method for a disease treatable by inhibiting PI3Kδ, comprising administering the crystal according to claim 21 to a subject in need of treatment for a disease treatable by inhibiting PI3Kδ.

24. The treatment method according to claim 23, wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

25. A crystal of a p-toluenesulfonic acid salt of [2-(1-methyl-1H-pyrazol-4-yl)-6-(morpholin-4-yl)-9H-purin-8-yl][4-(morpholin-4-yl)piperidin-1-yl]methanone having at least 5 peaks at diffraction angles (2θ) selected from 2.8±0.2, 5.6±0.2, 8.4±0.2, 11.2±0.2, 15.0±0.2, 21.4±0.2, 22.9±0.2 and 25.7±0.2 in powder X-ray diffraction using CuKα radiation.

26. A pharmaceutical composition comprising the crystal according to claim 25 and a pharmaceutically acceptable additive.

27. A treatment method for a disease treatable by inhibiting PI3Kδ, comprising administering the crystal according to claim 25 to a subject in need of treatment for a disease treatable by inhibiting PI3Kδ.

28. The treatment method according to claim 27, wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

29. A crystal of a citric acid salt of [2-(1-methyl-1H-pyrazol-4-yl)-6-(morpholin-4-yl)-9H-purin-8-yl][4-(morpholin-4-yl)piperidin-1-yl]methanone having at least 6 peaks at diffraction angles (2θ) selected from 6.5±0.2, 9.5±0.2, 10.6±0.2, 14.5±0.2, 15.1±0.2, 17.0±0.2, 20.7±0.2 and 26.3±0.2 in powder X-ray diffraction using CuKα radiation.

30. A pharmaceutical composition comprising the crystal according to claim 29 and a pharmaceutically acceptable additive.

31. A treatment method for a disease treatable by inhibiting PI3Kδ, comprising administering the crystal according to claim 29 to a subject in need of treatment for a disease treatable by inhibiting PI3Kδ.

32. The treatment method according to claim 31, wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

33. A crystal of a citric acid salt of [2-(1-methyl-1H-pyrazol-4-yl)-6-(morpholin-4-yl)-9H-purin-8-yl][4-(morpholin-4-yl)piperidin-1-yl]methanone having at least 6 peaks at diffraction angles (2θ) selected from 4.5±0.2, 6.4±0.2, 9.1±0.2, 10.2±0.2, 13.5±0.2, 14.5±0.2, 16.9±0.2 and 25.8±0.2 in powder X-ray diffraction using CuKα radiation.

34. A pharmaceutical composition comprising the crystal according to claim 33 and a pharmaceutically acceptable additive.

35. A treatment method for a disease treatable by inhibiting PI3Kδ, comprising administering the crystal according to claim 33 to a subject in need of treatment for a disease treatable by inhibiting PI3Kδ.

36. The treatment method according to claim 35, wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

37. A crystal of an oxalic acid salt of [2-(1-methyl-1H-pyrazol-4-yl)-6-(morpholin-4-yl)-9H-purin-8-yl][4-(morpholin-4-yl)piperidin-1-yl]methanone having at least 5 peaks at diffraction angles (2θ) selected from 3.2±0.2, 11.6±0.2, 15.2±0.2, 16.6±0.2, 16.9±0.2, 22.5±0.2, 25.3±0.2 and 26.1±0.2 in powder X-ray diffraction using CuKα radiation.

38. A pharmaceutical composition comprising the crystal according to claim 37 and a pharmaceutically acceptable additive.

39. A treatment method for a disease treatable by inhibiting PI3Kδ, comprising administering the crystal according to claim 37 to a subject in need of treatment for a disease treatable by inhibiting PI3Kδ.

40. The treatment method according to claim 39, wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

41. A crystal of a glutaric acid salt of [2-(1-methyl-1H-pyrazol-4-yl)-6-(morpholin-4-yl)-9H-purin-8-yl][4-(morpholin-4-yl)piperidin-1-yl]methanone having at least 5 peaks at diffraction angles (2θ) selected from 5.6±0.2, 8.7±0.2, 11.2±0.2, 17.5±0.2, 18.4±0.2, 21.5±0.2, 22.7±0.2 and 24.9±0.2 in powder X-ray diffraction using CuKα radiation.

42. A pharmaceutical composition comprising the crystal according to claim 41 and a pharmaceutically acceptable additive.

43. A treatment method for a disease treatable by inhibiting PI3Kδ, comprising administering the crystal according to claim 41 to a subject in need of treatment for a disease treatable by inhibiting PI3Kδ.

44. The treatment method according to claim 43, wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

45. A crystal of a malic acid salt of [2-(1-methyl-1H-pyrazol-4-yl)-6-(morpholin-4-yl)-9H-purin-8-yl][4-(morpholin-4-yl)piperidin-1-yl]methanone having at least 5 peaks at diffraction angles (2θ) selected from 4.6±0.2, 9.3±0.2, 9.6±0.2, 14.1±0.2, 15.4±0.2, 20.6±0.2, 25.0±0.2 and 27.8±0.2 in powder X-ray diffraction using CuKα radiation.

46. A pharmaceutical composition comprising the crystal according to claim 45 and a pharmaceutically acceptable additive.

47. A treatment method for a disease treatable by inhibiting PI3Kδ, comprising administering the crystal according to claim 45 to a subject in need of treatment for a disease treatable by inhibiting PI3Kδ.

48. The treatment method according to claim 47, wherein the disease is psoriasis, psoriatic arthritis, rheumatoid arthritis, allergic asthma, severe asthma, steroid resistant asthma, chronic obstructive pulmonary disease (COPD), systemic lupus erythematosus, primary immunodeficiency syndrome or cancer.

* * * * *

UNITED STATES PATENT AND TRADEMARK OFFICE
CERTIFICATE OF CORRECTION

PATENT NO. : 10,822,336 B2
APPLICATION NO. : 16/337664
DATED : November 3, 2020
INVENTOR(S) : Y. Ueda et al.

It is certified that error appears in the above-identified patent and that said Letters Patent is hereby corrected as shown below:

On the Title Page

| Column | Line | |
|---|---|---|
| 1/Title | 3 | Please change "6(" to -- 6-( --. |
| 1/Assignee | 2 | Please change "Tokyo" to -- Chuo-ku Tokyo --. |

In the Specification

| Column | Line | |
|---|---|---|
| 1/Title | 3 | Please change "6(" to -- 6-( --. |

Signed and Sealed this
Twenty-fourth Day of May, 2022

Katherine Kelly Vidal
*Director of the United States Patent and Trademark Office*